US007906488B2

(12) United States Patent
Nieuwenhuizen

(10) Patent No.: US 7,906,488 B2
(45) Date of Patent: Mar. 15, 2011

(54) SPHINGOLIPIDS IN TREATMENT AND PREVENTION OF STEATOSIS AND OF STEATOSIS OR OF HEPATOTOXICITY AND ITS SEQUELAE

(75) Inventor: Willem Ferdinand Nieuwenhuizen, Bunnik (NL)

(73) Assignee: Nederlandse Organisatie Voor Toegepast-Natuurwetenschappelijk Onderzoek Tno, Delft (NL)

( * ) Notice: Subject to any disclaimer, the term of this patent is extended or adjusted under 35 U.S.C. 154(b) by 214 days.

(21) Appl. No.: 11/791,876

(22) PCT Filed: Nov. 25, 2005

(86) PCT No.: PCT/NL2005/000813
§ 371 (c)(1),
(2), (4) Date: Jan. 24, 2008

(87) PCT Pub. No.: WO2006/059897
PCT Pub. Date: Jun. 8, 2006

(65) Prior Publication Data
US 2008/0182902 A1 Jul. 31, 2008

(30) Foreign Application Priority Data

Nov. 30, 2004 (EP) .................................... 04078265
Apr. 12, 2005 (EP) .................................... 05075856
Sep. 6, 2005 (EP) .................................... 05077029

(51) Int. Cl.
*A61K 31/70* (2006.01)
*A61K 31/66* (2006.01)
*A61K 31/22* (2006.01)

(52) U.S. Cl. ............ 514/23; 514/114; 514/119; 514/551
(58) Field of Classification Search .................... 514/23, 514/114, 119, 551
See application file for complete search history.

(56) References Cited

U.S. PATENT DOCUMENTS

| 5,190,876 A | 3/1993 | Kinkade, Jr. et al. |
| 5,232,837 A | 8/1993 | Merrill, Jr. et al. |
| 5,374,616 A | 12/1994 | Spiegel et al. |
| 5,478,860 A | 12/1995 | Wheeler et al. |
| 5,519,007 A | 5/1996 | Della Valle et al. |
| 5,830,853 A | 11/1998 | Baeckstroem et al. |
| 6,562,606 B1 | 5/2003 | Elias et al. |
| 6,610,835 B1 | 8/2003 | Liotta et al. |
| 2001/0011076 A1 | 8/2001 | Schwartz et al. |
| 2002/0110587 A1 | 8/2002 | Rodrigueza et al. |
| 2002/0182250 A1 | 12/2002 | Hori et al. |
| 2003/0049286 A1 | 3/2003 | Granger et al. |
| 2003/0109044 A1 | 6/2003 | Logan et al. |
| 2004/0047851 A1 | 3/2004 | Tabas et al. |
| 2004/0063667 A1 | 4/2004 | Kishikawa et al. |
| 2004/0147615 A1 | 7/2004 | Rinehart et al. |
| 2004/0171557 A1 | 9/2004 | Iian et al. |
| 2007/0010483 A1* | 1/2007 | Iian et al. ........................ 514/54 |
| 2007/0098808 A1 | 5/2007 | Sampalis |

FOREIGN PATENT DOCUMENTS

| DE | 196 02 108 | 7/1997 |
| EP | 0 373 038 | 6/1990 |
| EP | 0 988 860 | 3/2000 |
| EP | 1 291 340 | 3/2003 |
| EP | 1 452 181 | 9/2004 |
| FR | 2 492 259 A | 4/1982 |
| FR | 2 820 037 A | 8/2002 |
| JP | 61 152632 | 7/1986 |
| JP | 63 044842 A | 2/1998 |
| JP | 11 269074 | 10/1999 |
| JP | 2000/350563 | 12/2000 |
| JP | 2001/158735 | 6/2001 |
| JP | 2001/158736 | 6/2001 |
| JP | 2001 213858 A | 8/2001 |
| JP | 2002/068998 | 3/2002 |
| JP | 2002/226394 | 8/2002 |
| JP | 2003 137894 | 5/2003 |
| KR | 2001 008 569 A | 2/2001 |
| WO | WO 92/03129 | 3/1992 |
| WO | WO 95/32002 | 11/1995 |
| WO | WO 97/11706 A | 4/1997 |
| WO | WO 99/41266 A | 8/1999 |
| WO | WO 99/61581 | 12/1999 |

(Continued)

OTHER PUBLICATIONS

Barenholz et al. (Biochemistry, vol. 7, No. 7, pp. 2603-2609; 1968).*
Patani et al. (Chem Rev, vol. 96, No. 8, pp. 3147-3176; 1996).*
Haller (Z Gesamte Inn Med, vol. 32, No. 8, pp. 124-128; 1977).*
Stella (Expert Opinion on Therapeutic Patents, Prodrugs as therapeutics, vol. 14, No. 3, pp. 277-280; 2004).*
Wolff (Burger's Medicinal Chemistry, 5th Ed., vol. 1, pp. 975-977; 1994).*
Testa (Biochemical Pharmacology, Prodrug Research: futile or fertile?, vol. 68, pp. 2097-2106; 2004).*
Ettmayer et al. (Medicinal Chemistry, Lessons Learned from Marketed and Investigational Prodrugs, vol. 47, No. 10, pp. 2394-2404; 2004).*

(Continued)

*Primary Examiner* — Raymond J Henley, III
(74) *Attorney, Agent, or Firm* — Weingarten, Schurgin, Gagnebin & Lebovici LLP

(57) ABSTRACT

The present invention relates to the use of sphingolipids for the preparation of a food item, a food supplement and/or a medicament for the prevention and/or treatment of elevated blood levels of cholesterol and triglycerides related to steatosis and hepatotoxic effects of medicaments and viral infections. In particular, the invention relates to the use of a sphingolipid such as phytosphingosine, sphingosine, sphinganine, ceramide, glycosylceramide and/or sphingomyelin, or a precursor or a derivative of a sphingolipid, or a pharmaceutically acceptable salt thereof, for the prevention and/or treatment of hepatotoxic effects such as hepatic steatosis, fibrosis and/or cirrhosis.

(I)
$$R_1-(A)_t-CH_2-CH\underset{Q_1-R_2}{\overset{OH}{-}}CH-Z$$

6 Claims, 7 Drawing Sheets

FOREIGN PATENT DOCUMENTS

| | | |
|---|---|---|
| WO | WO 00/50574 | 8/2000 |
| WO | WO 01/60807 | 8/2001 |
| WO | WO 01/72701 | 10/2001 |
| WO | WO 02/34062 | 5/2002 |
| WO | WO 02/102394 | 12/2002 |
| WO | WO 03/011873 | 2/2003 |
| WO | WO 03/088761 | 10/2003 |
| WO | WO 03/096983 | 11/2003 |
| WO | WO 2004/016257 | 2/2004 |
| WO | WO 2004/064819 | 8/2004 |
| WO | WO 2004/064820 | 8/2004 |
| WO | WO 2004/064823 | 8/2004 |
| WO | WO 2004/096140 | 11/2004 |

OTHER PUBLICATIONS

The Merck Manual ([online], www.merck.com [Retrieved on Jun. 20, 2009 from the Internet: <URL: http://www.merck.com/mmhe/sec10/ch136/ch136b.html?qt=hepatic%20steatosis&alt=sh]).*

Auge, Nathalie et al.: "Sphingomyelin metabolites in vascular cell signaling and atherogensis" Progress in Lipid Research, vol. 39, No. 3, May 2000, pp. 207-229.

Beers, M.H. and R. Berkow: "The Merck Manual of Diagnosis and Therapy, seventeenth edition" 1999, Merck Research Laboratories, Whitehouse Station, N.J., XP002311213 p. 1655, col. 1, paragraph 4—p. 1656, col. 1, paragraph 3.

Beers, M.H. and R. Berkow: "The Merck Manual of Diagnosis and Therapy, seventeenth edition" 1999, Merck Research Laboratories, Whitehouse Station, N.J., XP002341450 p. 1062; tables 148-4.

Bibel, D. J. et al.: "Antimicrobial Activity of Sphingosines" Journal of Investigative Dermatology, vol. 98, No. 3, 1992, pp. 269-273.

Bischoff, A. et al.: "Sphingosine-1-Phosphate and sphingosylphosphorylcholine constrict renal and mesenteric microvessels in vitro" British Journal of Pharmacology, Basingstoke, Hants, GB, vol. 130, No. 8, Aug. 2000, pp. 1871-1877.

Chatterjee, Subroto: "Sphingolipids in atherosclerosis and vascular biology" Arteriosclerosis Thrombosis and Vascular Biology, vol. 18, No. 10, Oct. 1998, pp. 1523-1533.

Chong, P.H. et al.: "Atorvastatin calcium: an addition to HMG-CoA reductase inhibitors." Pharmacotherapy, vol. 17(6), pp. 1157-1177; 1997.

Chung, N. et al.: "Phytosphingosine as a specific inhibitor of growth and nutrient import in Saccharomyces cerevisiae." The Journal of Biological Chemistry. United States Sep. 21, 2001, vol. 276, No. 38, pp. 35614-35621.

Davaille et al. 2000. J. Biol. Chem., vol. 275, No. 44, pp. 34628-34633.

Fantini, J. et al.: "Synthetic Soluble Analogs of Galactosylceramide (GalCer) Bind to the V3 Domain of HIV-1 gp120 and Inhibit HIV-1-induced Fusion and Entry" Journal of Biological Chemistry, vol. 272, No. 11, 1997, pp. 7245-7252.

Howell et al. 2002. Current Organic Chemistry, vol. 6, No. 4, 2002, pp. 365-391.

Jiang, Xian-Cheng et al.: "Plasma sphingomyelin level as a risk factor for coronary artery disease" Arteriosclerosis Thrombosis and Vascular Biology, vol. 20, No. 12, Dec. 2000, pp. 2614-2618.

Jung et al. 1996. Journal of Natural Products, vol. 59, No. 3, pp. 319-322.

Kim, et al. 2000. Phytotherapy Res., 14(6), 448-451.

Leventhal, A. R. et al.: "Acid sphingomyelinase-deficient macrophages have defective cholesterol trafficking and efflux." The Journal of Biological Chemistry. Nov. 30, 2001, vol. 276, No. 48, pp. 44976-44983.

Mei Jie et al.: "$C_2$—Ceramide influences the expression and insulin-mediated regulation of cyclic nucleotide phosphodiesterase 3B and lipolysis in 3T3-I1 adipocytes." Diabetes, vol. 51(3), pp. 631-637; 2002.

Merrill Jr., A. H. et al.: "Role of dietary sphingolipids and inhibitors of sphingolipid metabolism in cancer and other diseases" Journal of Nutrition 1995 United States, vol. 125, No. 6 Suppl., pp. 1677S-1682S.

Ortenberg et al: Farmakologiya i Toksikologiya (Moscow), vol. 47, No. 4, 1984, pp. 102-105.

Rueda, R. et al.: "Addition of gangliosides to an adapted milk formula modifies levels of fecal Escherichia coli in preterm newborn infants" J. Pediatr., vol. 133, 1998, pp. 90-94.

Schmelz, E. M. et al.: "Sphingomyelin consumption suppresses aberrant colonic crypt foci and increases the proportion of adenomas versus adenocarcinomas in cf1 mice treated with 1,2-dimethylhydrazine: implications for dietary sphingolipids and colon carcinogenesis" Cancer Research, American Association for Cancer Research, Baltimore, MD, US, vol. 56, No. 21, Nov. 1, 1996, pp. 4936-4941.

Sosnowski et al. 1997. Journal of Urology, vol. 158, No. 1, pp. 269-274.

Sprong, R.C. et al.: "Bovine milk fat components inhibit food-borne pathogens." International Dairy Journal, vol. 12, pp. 209-215, 2002.

Thurman et al. 1994. Transplant Int.: Off. J. Eur. Soc. For Organ Transplantation. 1994, vol. 7 suppl 1, pp. s167-s170.

Turinsky J et al: "Effect of sphingoid bases on basal and insulin-induced glucose uptake by skeletal muscle", Journal of Cell Biology, vol. 115, No. 3 Part 2, 1991, p. 222A; & abstracts of papers presented at the thirty-first annual meeting of the american society for cell bi.

Van Veldhoven Paul P et al: "Do sphingoid bases interact with the peroxisome proliferator activated receptor alpha (PPAR-alpha)?"; Cellular Signaling, vol. 12, No. 7, Jul. 2000, pp. 475-479.

Vesper, H. et al.: "Sphingolipids in Food and the Emerging Importance of Sphingolipids to Nutrition" Journal of Nutrition, vol. 129, 1999, pp. 1239-1250.

Viola, G. et al.: "Absorption and distribution of arachidonate in rats receiving lysophospholipids by oral route" Journal of Lipid Research, Bethesda, MD, US, vol. 34, No. 11, 1993, pp. 1843-1852.

Yamada, T. et al.: "Growth inhibition of pancreatic cancer cells by sphingosylphosphorylcholine and influence of culture conditions" CMLS, Cell. mol. life. sci. vol. 53, pp. 435-441, 1997.

Zheng et al. 2002. Hepatology, vol. 36, No. 4 part 2, p. 215a. Abstract No. 196.

Turinsky J. et al: "Effect of sphingoid bases on basal and insulin-induced glucose uptake by skeletal muscle", Journal of Cell Biology, vol. 115, No. 3 Part 2, 1991, p. 222A; & abstracts of papers presented at the thirty-first annual meeting of the American Society for Cell Biology, Boston, Massachusetts, USA.

* cited by examiner

SPHINGOLIPIDS IN TREATMENT AND PREVENTION OF STEATOSIS AND OF STEATOSIS OR OF HEPATOTOXICITY AND ITS SEQUELAE

This application is a §371 national phase filing of PCT/NL2005/000813 filed Nov. 25, 2005; and claims priority to three European applications:
EP 04 078265.8 filed Nov. 30, 2004; and
EP 05 075856.4 filed Apr. 12, 2005; and
EP 05 077029.6 filed Sep. 6, 2005.

TECHNICAL FIELD

The invention relates to preparations for the treatment and prevention of steatosis and hepatotoxic effects of elevated blood levels of cholesterol and triglycerides, medicaments and viral infections. In particular, the present invention relates to the use of sphingolipids, more preferably phytosphingosine, sphingosine, sphinganine, ceramide, glycosylceramide and/or sphingomyelin for the preparation of a food item or a medicament for the prevention and/or treatment of hepatic damage such as hepatic steatosis, fibrosis and/or cirrhosis.

BACKGROUND OF THE INVENTION

The liver plays an important role in the metabolism of fat in the body. Via the production of bile fluid, the liver is actively involved in the degradation of fat. In addition, the liver may take up and break down fats and is involved in the de novo production of fats, such as triglycerides and cholesterol. In case of a disturbance in the fat metabolism in the liver, fat may accumulate in the liver cells. This excessive accumulation or storage of lipids in the liver is called hepatic steatosis or liver steatosis. From a simple storage of excess lipid, hepatic steatosis can progress to steatohepatitis, or inflammatory hepatic lipid storage, possibly due to oxidative stress and lipid peroxidation. Finally, this will result in hepatocellular injury, progressive hepatic fibrosis (scarring) and cirrhosis, and finally liver failure. Hepatic steatosis may be diagnosed by investigating liver secretion products in blood, by echographical investigation of the liver, by imaging techniques such as MRI and CT scan, or by performing a liver function. Hepatotoxic compounds and viral infections may lead to steatosis and eventually cirrhosis by disturbing the lipid metabolism of the liver.

The triglyceride content of hepatocytes is regulated by the integrated activities of cellular molecules that facilitate hepatic triglyceride uptake, fatty acid synthesis, and esterification on the one hand ("input") and hepatic fatty acid oxidation and triglyceride export on the other ("output"). Steatosis occurs, when "input" exceeds the capacity for "output". The liver acts in concert with other organs in the orchestration of inter-organ fatty acid/triglyceride partitioning. There is a continuous cycling and redistribution of non-oxidised fatty acids between different organs especially in the post-absorptive state, with a central role for the liver and the adipose tissue.

Hence, the amount of liver triglyceride content is not fixed, but can readily be modulated by nutritional conditions in otherwise normal livers. In addition, intrinsically normal livers may also develop steatosis due to metabolic and endocrine interactions involving both interorgan triglyceride/free fatty acid partitioning and triglyceride/free fatty acid metabolism. Next to extra-hepatic causes for hepatic steatosis, several intrahepatic mechanisms inducing steatosis exist. Increased de novo hepatic synthesis of fatty acids and subsequent esterification into triglycerides may also be an important cause of steatosis.

Hepatic steatosis was in the past often exclusively thought of as the result of alcohol abuse. However, hepatic steatosis is now known to be of much wider occurrence. For instance, hepatic steatosis can often be diagnosed in individuals with truncal obesity, type 2 diabetes, hypertriglyceridemia and other features of the so called metabolic syndrome or syndrome X. Also, chronic infection with hepatitis C virus and many medicaments regularly results in toxic effects on the liver and hepatic steatosis. Epidemiological studies in humans have documented an association between visceral obesity and cardiovascular risk factors such as dyslipidaemia, insulin resistance and type 2 diabetes mellitus. Recently, attention has been focused on the excessive accumulation of triglycerides (TG) within the liver as part of this metabolic syndrome. It appears that fat accumulation in the liver is associated with several features of insulin resistance even in normal-weight and moderately overweight subjects. Nonetheless, from these observations in humans it remains unclear to what extent hepatic steatosis is a cause rather than a consequence of the metabolic syndrome. Therefore, the view should be changed that hepatic steatosis is to be regarded as a benign, in itself innocent, aspect of a disease. Rather, it may be regarded upon as a premorbid condition that often progresses to advanced liver disease. The liver enzyme Alanine Amino Transferase (abbreviated as ALT in human and ALAT in mice) concentration in blood is used to monitor early stages of liver damage caused by hepatotoxic compounds and the development of steatosis. A low ALT can therefore be considered as healthy.

Almost 1000 pharmaceutical agents are recognized to cause hepatotoxicity, and drug-induced liver toxicity accounts for approximately 15-25% of fulminant hepatic failure cases and nearly 2000 deaths annually in the United States [H. J. Zimmerman, The spectrum of hepatotoxicity, in: Hepatotoxicity: The Adverse Effects of Drugs and other Chemicals on the Liver, second ed., Lippincott Williams & Wilkins, Philadelphia, 1999, pp. 3-11]. Therefore, there is at present a need for medicaments or food items for the prevention and/or treatment of hepatotoxic effects of medicaments, viral infections and high cholesterol and triglyceride concentrations, leading to steatosis, and to prevent the more damaging consequences thereof, in particular medicaments or food items for the prevention and/or treatment of hepatic fibrosis and hepatic cirrhosis are sought after.

SUMMARY OF THE INVENTION

In relation thereto, the present inventors have now found that food items and clinically safe medicaments comprising sphingolipids may very suitably be used for preventing the development of steatosis and/or to alleviate the severity of steatosis and to alleviate the hepatotoxic effects of medicaments and viral infections. As a result, the food items and clinically safe medicaments comprising sphingolipids may suitably be used to prevent the occurrence of the more damaging consequences of the damaging effects on liver function, in particular steatosis. Due to this capacity, the food items and medicaments comprising sphingolipids may be used in accordance with the present invention for the prevention and/or treatment of liver damage such as hepatic steatosis as well as to disorders directly resulting therefrom such as hepatic fibrosis and hepatic cirrhosis. In several groups of at-risk patients, such as diabetes type 2 patients, steatosis may also occur in the heart muscle or in other muscles and compositions comprising sphingolipids may therefore also be used to prevent and/or treat these forms of steatosis. Preferably hepatic steatosis is prevented and/or treated.

In one aspect the invention now provides the use of a sphingolipid according to the formula (I)

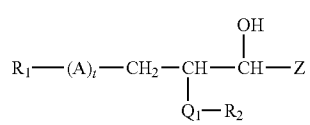
(I)

wherein
Z is $R_3$ or —CH(OH)—$R_3$;
A is sulphate, sulphonate, phosphate, phosphonate or —C(O)O—;
$R_1$ is H, hydroxyl, alditol, glycosyl, alcohol, $C_1$-$C_6$ alkyl or amino acid;
$R_2$ is H or unsaturated or saturated ($C_1$-$C_{30}$) alkyl chain;
$R_3$ is unsaturated or saturated ($C_1$-$C_{30}$) alkyl chain;
$Q_1$ is a primary amine group (—$NH_2$), secondary amine group (—NH—) or an amide group (—NH—CO—); preferably an secondary amine group; and t is 0 or 1, or a precursor, a derivative or a pharmaceutically acceptable salt thereof for the manufacture of a medicament for the prevention and/or treatment hepatic steatosis and/or disorders directly resulting therefrom such as (steatosis-induced) fibrosis and (steatosis-induced) cirrhosis, more preferably hepatic steatosis itself.

In a preferred embodiment of said use, said sphingolipid is a sphingolipid according to the formula (I), wherein $R_1$ is H, hydroxyl, alditol, alcohol, $C_1$-$C_6$ alkyl, amino acid or a glycosyl selected from the group consisting of acesulfam, allose, altrose, arabinose, erythrose, fructose, fucose, galactose, gulose, idose, isomaltose, lactose, lyxose, maltose, mannose, melezitose, psicose, raffinose, rhamnose, ribose, saccharose, sorbose, stachyose, sucrose, tagatose, talose, threose, trehalose, turanose, xylose and xylulose;

In another preferred embodiment of said use, said sphingolipid is a sphingolipid according to the formula (I), wherein $R_1$ is H, hydroxyl, alditol, alcohol, $C_1$-$C_6$ alkyl or amino acid;

In yet another preferred embodiment of said use, said sphingolipid is a sphingolipid according to the formula (I), wherein, in the case that Q1-R2 is the primary amine group and R1 is H, A is selected from sulphate, sulphonate, —C(O)O—, and phosphonate.

In yet another preferred embodiment of said use, said sphingolipid is a sphingolipid according to the formula (I), wherein $R_1$ is H, hydroxyl, alditol, alcohol, $C_1$-$C_6$ alkyl or amino acid;

In another preferred embodiment of said use, said sphingolipid is a sphingolipid according to the formula (II)

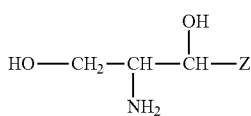
(II)

wherein
Z is $R_3$ or CH(OH)—$R_3$ and $R_3$ is an unsaturated or saturated ($C_1$-$C_{30}$) alkyl chain.

In a still further preferred embodiment of said use, said sphingolipid is a sphingolipid according to formula (III)

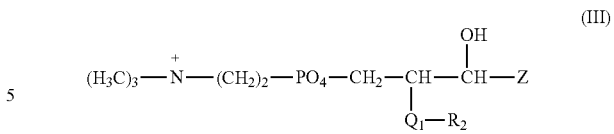
(III)

wherein
Z is $R_3$ or CH(OH)—$R_3$, preferably $R_3$, and $R_3$ is an unsaturated or saturated ($C_1$-$C_{30}$) alkyl chain, preferably $R_3$ is an unsaturated ($C_1$-$C_{30}$) alkyl chain;
$Q_1$ is a primary amine group (—$NH_2$), a secondary amine group (—NH—) or an amide group (—NH—CO—); preferably an amine group, and
$R_2$ is H or unsaturated or saturated ($C_1$-$C_{30}$) alkyl chain.

In highly preferred embodiments, wherein the sphingolipid is a sphingolipid according to the formula (II), a sphingolipid for use in aspects of the present invention is phytosphingosine, sphinganine or sphingosine, and in a still more preferred embodiment said sphingolipid is phytosphingosine.

In other highly preferred embodiments, the sphingolipid is a sphingolipid according to the formula (IV),

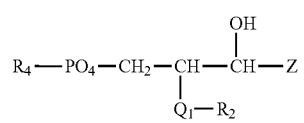
(IV)

wherein
Z, $Q_1$, and $R_2$ are as defined above, and
$R_4$ is selected from H, hydroxyl, alditol, glycosyl, alcohol, $C_1$-$C_6$ alkyl or amino acid, provided that when $R_4$ is H, Q1-$R_2$ is not the primary amine group. The hydroxyl, alditol, alcohol, $C_1$-$C_6$ alkyl or amino acid can for instance be those compounds as named for $R_1$ above. In case $R_4$ is glycosyl, it may be selected from the group of radicals consisting of acesulfam, allose, altrose, arabinose, erythrose, fructose, fucose, galactose, glucose, gulose, idose, isomaltose, lactose, lyxose, maltose, mannose, melezitose, psicose, raffinose, rhamnose, ribose, saccharose, sorbose, stachyose, sucrose, tagatose, talose, threose, trehalose, turanose, xylose and xylulose, and other mono-, di-, or polysaccharides.

The present invention also provides use of a sphingolipid according to the formula (I), (II), (III) or (IV) or a precursor or a derivative as a liver protective agent, a steatosis-preventing agent, preferably a hepatic steatosis-preventing agent. Such an agent may very suitably be used in food items and pharmaceutical compositions to that effect. Thus, the present invention provides the use of a sphingolipid as defined herein as a liver protective agent and in particular as an antisteatotic agent for the management of steatosis, preferably steatosis of the liver. The present invention also provides the use of a sphingolipid as defined herein as an antifibrotic agent for the management of liver fibrosis, and in general as an effective agent for liver protection, or as hepato-protective agent. Such protective effects include the protection against the steatotic side-effects of HIV inhibitors and other medicaments on the liver. The liver-protecting effects for instance also include the protection against liver damage as a result of (excessive) alcohol consumption, viral infections and the use of hepato-toxic medicaments. In fact, the hepato-protective effect in accordance with the present invention is not limited to any specific cause of the steatosis. Therefore, in general it should be noted that also metabolic imbalances or other cellular disorders that form the underlying mechanism and that ultimately result in the accumulation of fat and the development of steatosis may be prevented and/or treated by uses and methods according to the invention. The uses provided herein include both medical and non-medical uses. In several instances, such as in food items and in diet formulations the non-medical application is preferred. In that case the use is directed to the non-medical dietary use of the hepato-protective effects, including the hepatic steatosis-preventing effects. Very suitable uses include the use as a non-prescriptive food or dietary supplement.

In another aspect, the present invention relates to the use of a sphingolipid according to the formula (I), (II), (III) or (IV) or a precursor or a derivative for the manufacture of a food item or food supplement capable of preventing hepatotoxic effects and steatosis in a subject, and preferably hepatic steatosis, fibrosis and/or cirrhosis.

In another aspect, the present invention provides a method of preventing the occurrence of hepatic steatosis, fibrosis and/or cirrhosis in a healthy subject comprising providing said subject a diet with enhanced levels of a sphingolipid according to the formula (I), (II), (III) or (IV) or a precursor, a derivative or a pharmaceutically acceptable salt thereof. Typically such a diet may comprises a food item or food supplement capable of preventing hepatic steatosis, fibrosis and/or cirrhosis as defined herein.

In another aspect, the present invention provides a method of preventing hepatic steatosis, fibrosis and/or cirrhosis in a healthy subject comprising providing said subject a diet with enhanced levels of a sphingolipid according to the formula (I), (II), (III) or (IV) or a precursor, a derivative or a pharmaceutically acceptable salt thereof.

Since hepatic steatosis is a disease condition that may develop gradually in subjects at risk, the risk of developing hepatic steatosis as well as the progression thereof into hepatic fibrosis and hepatic cirrhosis may be diminished by the administration of a non-prescribed medicament, a food item or a food supplement to an at-risk subject by medically non-skilled persons. Many of the food items and food supplements, including nutraceuticals, of the present invention may be sold over-the-counter in health-food shops or chemist's. As such, in one preferred embodiment, the present invention relates to a method of preventing hepatotoxic effects of medicaments, virus infections, hepatic steatosis, fibrosis and/or cirrhosis in an at-risk subject as a non-medical method. Of course, such a method of prevention may alternatively comprise a method of preventing the occurrence of hepatic steatosis, fibrosis and/or cirrhosis in a healthy subject comprising administrating to said subject a therapeutically effective amount of a pharmaceutical composition comprising a sphingolipid according to the formula (I), (II), (III) or (IV) or a precursor, a derivative or a pharmaceutically acceptable salt thereof and a pharmaceutically acceptable carrier, and optionally one or more excipients.

The medicaments, pharmaceutical compositions and preparations of the present invention are preferably for oral administration.

In yet another aspect, the present invention provides a method of treatment of subjects suffering from liver damage including hepatic steatosis, fibrosis and/or cirrhosis, said method comprising administrating to subjects in need thereof a therapeutically effective amount of a pharmaceutical composition, said composition comprising a sphingolipid according to the formula (I), (II), (III) or (IV), or a precursor, a derivative or a pharmaceutically acceptable salt thereof and a pharmaceutically acceptable carrier, optionally one or more excipients and optionally one or more other pharmaceutically active compounds or medicaments.

In yet another aspect, the present invention provides the use of a food item with enhanced levels of a sphingolipid according to the formula (I), (II), (III) or (IV) or a precursor or a derivative thereof for the prevention and/or treatment of liver damage including hepatic steatosis, fibrosis and/or cirrhosis.

The use of food items, including food supplements and nutraceuticals, with enhanced levels of a sphingolipid according to the formula (I), (II), (III) or (IV) or a precursor or a derivative thereof, in any of the described methods of prevention and treatment is contemplated in the present invention.

The present invention further relates to the use of a pharmaceutical composition a sphingolipid according to the formula (I), (II), (III) or (IV) or a precursor or a derivative or a pharmaceutically acceptable salt thereof and a pharmaceutically acceptable carrier, and optionally one or more excipients, for the prevention and/or treatment of hepatic steatosis, fibrosis and/or cirrhosis.

The present invention further relates to a combined preparation of a sphingolipid as defined hereinabove or a precursor, a derivative or a pharmaceutically acceptable salt thereof and a medicament which is harmful to the liver, or is recognized as hepatotoxic or to cause drug-induced liver toxicity.

The present invention further relates to a pharmaceutical composition, said composition comprising a sphingolipid according to the formula (I), (II), (III) or (IV) or a precursor, a derivative or a pharmaceutically acceptable salt thereof, and at least one medicament which is harmful to the liver, or is recognized to cause hepatotoxicity or is known to cause drug-induced liver toxicity, said composition having the form of a combined preparation for simultaneous, separate or sequential use in the prevention and/or inhibition of liver disease, preferably in the prevention and/or inhibition of steatosis and/or disorders directly resulting therefrom. Preferably said steatosis is hepatic steatosis, and said disorders directly resulting therefrom are hepatic fibrosis and/or cirrhosis.

The present invention further relates to a combined preparation of a sphingolipid according to the formula (I), (II), (III) or (IV) or a precursor, a derivative or a pharmaceutically acceptable salt thereof and a medicament which is harmful to the liver, or is recognized as hepatotoxic or to cause drug-induced liver toxicity, for the simultaneous, separate or sequential use in therapy.

The present invention further relates to the use of a sphingolipid according to the formula (I), (II), (III) or (IV) or a precursor, a derivative or a pharmaceutically acceptable salt thereof, and a medicament which is harmful to the liver, or is recognized as hepatotoxic or to cause drug-induced liver toxicity, for the manufacture of a combined pharmaceutical preparation for simultaneous, separate or sequential use in the prevention and/or inhibition of liver disease, preferably for the prevention and/or inhibition of steatosis and/or disorders directly resulting therefrom. Preferably said steatosis is hepatic steatosis, and said disorders directly resulting therefrom are hepatic fibrosis and/or cirrhosis.

DEFINITIONS

Figure 1:
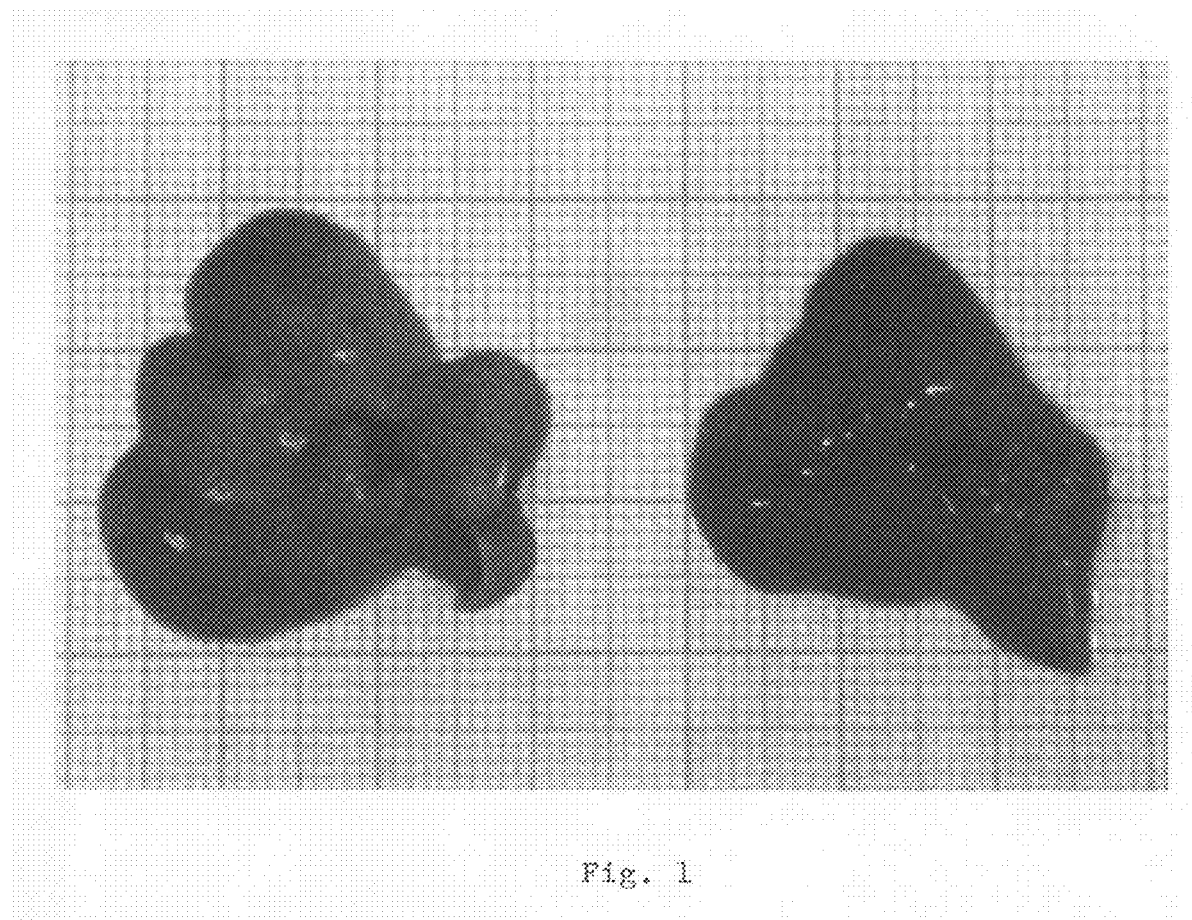
FIG. 1 shows the liver of a control-group animal fed a high fat high cholesterol diet (left) and the liver of an animal of a treatment group fed the same diet supplemented with 1% phytosphingosine (right) as described in Example 2. Note the marked difference in colour between the two livers, indicating the hepatic steatosis in the left liver.

As used herein "hepatotoxic" describes any internal or external influence which causes an impaired function of the liver, which is mainly characterised by an increase in the activity of the enzyme ALT. This hepatotoxicity can be caused by medication, by viral infection (hepatic fibrosis) and by the detrimental effect of fat accumulation in the liver, which is generally indicated by the term steatosis.

As used herein, the term "steatosis" refers to the condition in which fat accumulates in tissues, such as liver tissue, heart muscle tissue or other muscle tissues. The term "steatosis" does not imply any causative relationship with any metabolic condition or disorder.

As used herein, the term "liver damage directly resulting from steatosis" includes in general histological alteration, inflammation and cancer of the liver, and in particular includes such syndromes as steatohepatitis, hepatomegaly, hepatic cirrhosis, hepatic fibrosis, hepatocellular injury, hepatic inflammation, hepatocyte necrosis, liver failure or graft failure in the case of donor liver and liver cancer.

The term "preventing and/or treating the occurrence of steatosis" and the equivalent term "prevention and/or treatment of steatosis" refer to the uses and methods that include the prevention and/or treatment of the immediate underlying metabolic causes of steatosis such as the disordered metabolic and endocrine interactions in triglyceride metabolism in liver and heart muscle tissue, in particular in hepatocytes, and to the metabolic disorders non-alcoholic fatty liver disease (NAFLD) and non-alcoholic steatohepatitis (NASH).

As stated earlier, the term "hepatic steatosis" refers to the condition in which fat accumulates in the liver. As used herein, the term "hepatic steatosis" does not imply any causative relationship with any metabolic condition or disorder.

As used herein, the term "hepatic fibrosis" is used in its art-recognised meaning and refers to the clinically silent 'wound healing' process initiated in response to continuous insult to hepatic tissue. Globally, major causes are chronic Hepatitis B Virus (HBV) and Hepatitis C Virus (HCV) infection along with the metabolic disorders NAFLD/NASH. To date there are no approved antifibrotic agents for the management of fibrosis. Treatment is more focused on dealing with underlying conditions such as the use of antivirals for HBV/HCV and lifestyle changes for metabolic disorders. Chronic liver diseases (CLD) cause damage over a prolonged period of time, often in the complete absence of clinical symptoms, rendering early diagnosis and treatment extremely difficult. The disease follows a pathway consisting of several distinct stages. The initial liver inflammation, known as hepatitis, can be caused by a variety of insults of both infectious and non-infectious origin. Sustained hepatitis for longer than six months marks the progression to CLD, during which the liver initiates a scarring process similar to wound healing. This process, known as liver fibrosis, is characterized by the synthesis and accumulation of pathological fibrous tissue in the liver. Further exacerbation of fibrosis leads to cirrhosis, consisting in the alteration of the normal architecture of the liver with concomitant impairment of liver function. Ultimately, the affected patient either progresses to fulminant hepatic failure or develops a particular form of liver cancer, known as hepatocellular carcinoma (HCC).

As used herein, the term "hepatic cirrhosis" is used in its art-recognised meaning and refers to a group of chronic diseases of the liver in which normal liver cells are damaged and replaced by scar tissue, decreasing the amount of normal liver tissue. The distortion of the normal liver structure by the scar tissue interferes with the flow of blood through the liver. It also handicaps the function of the liver which, through the loss of normal liver tissue, leads to failure of the liver to perform some of its critically important functions. In liver cirrhosis the normal microcirculation, the gross vascular anatomy, and the hepatic architecture have been variably destroyed and altered with fibrous septa surrounding regenerated or regenerating parenchymal nodules.

As used herein, the term "sphingolipid" includes the generally accepted term for this particular lipid or lipid-like group of compounds, but it is specifically used to address the group of compounds according to the formulas (I), (II) and (III) of the present invention, including analogs or derivatives or pharmaceutically acceptable salts thereof, alone, or in combination, or as a so-called precursor compound, unless explicitly noted otherwise. The sphingolipids use in aspects of the present invention are used in non-complexed, non-bound form, i.e. in free form, not covalently linked to another (bio)molecule.

The term "elevated amount" (or "increased amount") relates to an amount of a component in a composition that is higher than the amount of component in the composition in nature or without human intervention, thus an amount above the naturally-occurring amount. The elevated amount of a component can be caused by addition of a component to a composition which normally does not contain said component, i.e. by enrichment of the composition with said component. An elevated amount of a component can also be caused by addition of a component to a composition which already contains said component, but which has, when the component is added, concentrations of the component which normally or naturally do not occur. Also this is called enrichment of the composition with the component.

Because of the variations in the amounts of sphingolipids (such as phytosphingosine, sphingosine, sphinganine, sphingomyelin, ceramide, glycosylceramide and lyso-sphingomyelin) in different food items no general values can be given for the amounts which will be indicated as "elevated amounts" according to the invention. For instance, a small amount of sphingomyelin in potato will be easily called an "elevated amount", because potato from itself does hardly contain any sphingomyelin. The same amount in milk, which normally does contain relatively high concentrations of sphingomyelin, will not give rise to the denomination of "elevated amount".

The terms "pharmaceutical compound", "(pharmaceutically) active compound", "(pharmaceutically) active substance", "therapeutic agent", "pharmaceutical agent", "medicament" and "drug" are used herein interchangeably.

The term "therapeutically effective amount" as used herein refers to an amount of a therapeutic agent to treat, ameliorate, or prevent a disease or condition, or to exhibit a detectable therapeutic or prophylactic effect. The precise effective amount needed for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation.

A "derivative", "analog" or "analogue" is defined herein as a sphingolipid according to the formula (I), (II), (III) or (IV) that is subjected to a (bio)chemical modification (e.g. organochemical or enzymatical). Derivatising may comprise the substitution of certain chemical groups to the sphingolipid, thereby retaining the sphingolipid character of the compound. Such derivatizations are known in the art. The derivatives and analogues maintain the biological activity of the natural sphingolipid and act in a comparable way, but may provide advantages to the molecule such as longer half-life, resistance to degradation or an increased activity. A very suitable derivative of phytosphingosine is for instance tetra acetyl phytosphingosine (TAPS, see below). Such a derivative may suitably be used in embodiments of the present invention since after hydrolysis, for instance in the body, the converted compound will exert its liver healing effects.

A "pharmaceutically acceptable salt" is defined herein as a salt wherein the desired biological activity of the sphingolipid is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base addition salts formed with metal cations such as zinc, calcium, bismuth, barium, magnesium, aluminium, copper, cobalt, nickel, cadmium, sodium, potassium and the like, or with a cation formed from ammonia, N,N-dibenzylethylene-diamine, D-glucosamine, tetraethylammonium or ethylenediamine; or (c) combinations of (a) and (b); e.g. a zinc tannate or the like. The use of a pharmaceutically acceptable salt of a sphingolipid according to the formula (I), (II), (III) or (IV), such as an ammonium salt or a chloride salt is preferred since the salt form is better soluble and will thus enhance the bio-availability of the sphingolipid. Preferably a salt of HCl is used. The use of a pharmaceutically acceptable salt is not limited to pharmaceutical preparations, but includes the use in food items or food supplements.

A "precursor" is defined herein as a derivative of the active compound with similar, less or no activity, and which can be transformed to the active compound e.g. by the digestive tract or other digestive systems in the body. Such precursors can be obtained by chemical or enzymatic modification of the active molecule.

"Subject" as used herein includes, but is not limited to, mammals, including, e.g., a human, non-human primate, mouse, pig, cow, goat, cat, rabbit, rat, guinea pig, hamster, horse, monkey, sheep, or other non-human mammal; and non-mammal animals, including, e.g., a non-mammalian vertebrate, such as a bird (e.g., a chicken or duck) or a fish, and an invertebrate.

DETAILED DESCRIPTION OF THE INVENTION

Sphingolipids are lipids of which some occur in food in low concentrations and which form a minor but important constituent of the cells of plants, animals and man. Since several sphingolipids occur naturally in the body of man and animal, they will be easily acceptable for addition to food and food compounds or as pharmaceutical agents.

Sphingolipids are generally composed of a long sphingoid base (sphingosine, sphinganine, phytosphingosine, or a related compound) as the central group of the molecule or "backbone" (see intra alia Karlsson. 1970. Chem. Phys. Lipids, 5:6-43), which may comprise an amide-linked long-chain fatty acid and a head group. There are hundreds of different molecular species of sphingolipids with different head groups (e.g. cholinephosphate, glucose, galactose, polysaccharides) and with different fatty acids and sphingoid bases (see intra alia Merrill & Sweeley. 1996. New Comprehensive Biochemistry Biochemistry of Lipids, Lipoproteins, and Membranes, (Vance, D. E. & Vance, J. E., eds.), pp. 309-338, Elsevier Science, Amsterdam).

The simplest sphingolipids, like sphingosine and sphinganine normally occur in food in very low concentrations. The richest sources of sphingolipids are dairy products, soy beans, eggs, meat, including fish meat, shellfish meat and meat of marine invertebrates, such as starfish. The most abundant sphingolipids in food are sphingomyelin (milk and eggs) and ceramide (meat). Whole milk contains predominantly sphingomyelin, but also contains glucosylceramide, lactosylceramide and gangliosides. Potato, apple, tomato, spinach, pepper and rice especially contain glycosylceramides in low concentration (see, e.g. Stryer L. 1988. Biochemistry, p. 287 [W.H. Freeman and Co., NY, USA]; Ryu J. et al. 2003. Arch Pharm Res. February; 26(2):138-42; Kawatake S, et al. 2002. Chem Pharm Bull (Tokyo) 50(8):1091-6).

It is known that sphingosine and sphingosine-analogs inhibit growth and metastasis of human and animal tumor cells (see e.g. EP 0 381 514). It is also known that administration of sphingomyelin to the food of rats can significantly decrease the chances of occurrence of malignant, chemically induced colon cancer.

Sphingolipids are also used in pharmaceutical compositions to protect skin and/or hair against the damaging effects of air pollution (see e.g. U.S. Pat. No. 5,869,034).

The antimicrobial action of sphingosine as a component of the skin against bacteria such as *Staphylococcus aureus*, *Candida albicans* and *Propionibacterium acnes* is known from dermatology (Bibel et al. 1992. J. Invest. Dermatol. 98(3): 269-73; Bibel et al. 1995. Clin Exp Dermatol 20(5):395-400), and the application of topical ointments comprising sphingosine is described therein.

WO 00/50574 discloses the use of anti-lipemic drugs comprising an effector of SREBP-1 associated with (linked to) a known serum cholesterol inhibitor such as fluvastatin, simvastatin, lovastatin for modulating serum cholesterol. Sphingomyelin and ceramide are disclosed as suitable effectors. However, an antisteatotic effect of sphingomyelin or ceramide in free form is not described.

US 2002/0182250 describes a lipid metabolism improving agent comprising a protein/phospholipid complex wherein the phospholipids is bound to the protein(hydrolysate) for use in the treatment or prevention of a variety of diseases including fatty liver. Sphingomyelin is mentioned amongst the phospholipids. However, it is not disclosed which of the ingredients of the agent is responsible for any of the claimed effects, and an antisteatotic effect of the free phospholipids is not described.

US 2004/0171557 describes that liver fat content in C57bI mice may be reduced by intraperitoneal injection of glucocerebroside. The oral administration of sphingolipids is however not disclosed herein.

WO 03/011873 discloses the use of a phospholipids-comprising extract of marine or aquatic crustaceans or zooplankton for treating a wide variety of disorders. Among the disorders presented are liver disease, steatosis and liver fibrosis. However, it is not disclosed in this prior art citation which of the many different ingredients of the extract is responsible for any of the claimed effects.

EP 1 452 181 describes the applicability of intermediary metabolites, such as glucosylceramides to threat various diseases. No reference is made to diseases of the liver.

Kim et al. (Phytotherapy Res. (2000) 14:448-451) describe the cerebroside LCC (1-O-(β-D-glucopyranosyl)-(2S,3R,4E,8Z)-2-N-palmityloctadecasphinga-4,8-diene) isolated from *Lycium chinense* as a potential hepatoprotective agent. Basis for this assumption is the observed ability of the compound to reduce the release into the culture medium of GPT and SDH from galactosamine-injured primary rat hepatocytes. No disclosure is made of a suitable use in the treatment and prevention of steatosis, i.e. of excessive fat accumulation in the liver of the whole organism.

The present inventors have now found that sphingolipids can be used effectively to prevent hepatotoxic effects such as caused by elevated plasma cholesterol and triglyceride concentrations, viral infections and medicaments, as indicated by elevated ALAT and SAA levels in plasma, and the development of hepatic steatosis and/or to alleviate the severity of hepatotoxic effects such as hepatic steatosis in a subject when such a sphingolipid is administered to said subject as, for instance, a food item, a food supplement or a medicament. Due to their capacity to prevent liver toxicity, the development of hepatic steatosis and/or to alleviate the severity of hepatic steatosis in a subject, the food items and medicaments of the present invention may also be used in the treatment and prevention of hepatic fibrosis resulting from said steatosis and of hepatic cirrhosis, resulting from said fibrosis. As a primary effect, steatosis (fat accumulation) is prevented. Moreover, in subjects at-risk of developing liver damage or disease, for instance as a result of the use of hepatotoxic substances (alcohol) or medicaments, overweight or obesity, health may be improved considerably by the use of sphingolipids according to the present invention and it is possible to prevent the occurrence of the clinical consequences of medicament use, virus infections, the Metabolic Syndrome or Syndrome X.

The alleviation of the severity of hepatic steatosis in a subject as a result of sphingolipid ingestion was observed in apoE*3-Leiden mice as outlined in the Examples below.

Thus according to the present invention, sphingolipids may be used for the manufacture of a food item or medicament for treating or preventing liver damage caused by hepatotoxicity of medicaments, high cholesterol and triglyceride levels, hepatic steatosis in a subject in need thereof, or in subjects suffering from or likely to develop hepatic steatosis as a result of alcohol abuse or in conjunction with diabetes type 2, or Metabolic Syndrome or Syndrome X, or as a result of side effects of (other) medicaments such as HIV inhibitors. The mechanism whereby this effect is achieved is not presently known, however, the finding has great impact for the prevention and/or treatment of disorders such as hepatic steatosis, fibrosis and cirrhosis, since, for the first time, food items and clinically safe medicaments can be prepared based on the sphingolipids, which food items and medicaments have the capacity to fight excessive accumulation of fat in the liver. Thus, food items and medicaments of the present invention, as well as their uses, are aimed at intervening early in the disease stage, i.e. at the level of accumulation of fat or steatosis, and thereby are able to prevent associated, more downstream disorders such as cirrhosis and fibrosis. The ability of the sphingolipids, as used in aspects of the present invention, to prevent excessive accumulation of fat was hitherto not described.

The present invention now provides in a first aspect the use of a sphingolipid according to the formula (I)

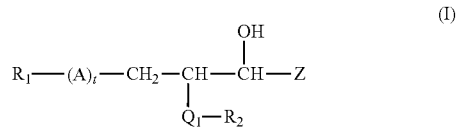

wherein
Z is $R_3$ or —CH(OH)—$R_3$;
A is sulphate, sulphonate, phosphate, phosphonate or —C(O)O—;
$R_1$ is H, hydroxyl, alditol, glycosyl, an alcohol, $C_1$-$C_6$ alkyl or amino acid;
$R_2$ is H or unsaturated or saturated ($C_1$-$C_{30}$) alkyl chain;
$R_3$ is unsaturated or saturated ($C_1$-$C_{30}$) alkyl chain;
$Q_1$ is a primary amine group (—$NH_2$), secondary amine group (—NH—) or an amide group (—NH—CO—); preferably an secondary amine group; and t is 0 or 1, or a precursor, a derivative or a pharmaceutically acceptable salt thereof for the manufacture of a medicament for the prevention and/or treatment of hepatic steatosis, fibrosis and cirrhosis.

$R_1$ can be selected from glycosyl radicals, preferably $R_1$ is selected from the group of radicals consisting of acesulfam, allose, altrose, arabinose, erythrose, fructose, fucose, galactose, gulose, idose, isomaltose, lactose, lyxose, maltose, mannose, melezitose, psicose, raffinose, rhamnose, ribose, saccharose, sorbose, stachyose, sucrose, tagatose, talose, threose, trehalose, turanose, xylose and xylulose.

$R_1$ is preferably selected from amino acids radicals, such as radicals of alanine, arginine, asparagines, aspartate, carnitine, citrulline, cysteine, cystine, GABA, glutamate, glutamine, gluthathione, glycine, histidine, hydroxyproline, isoleucine, leucine, lysine, methionine, ornithine, phenylalanine, proline, serine, taurine, threonine, tryptophane, tyrosine and valine or derivatives or combinations thereof.

$R_1$ is more preferably selected from the group consisting of hydrogen, hydroxyl or hydroxyl-containing group (e.g. hydroxyalkyl), alditol radical or polyol radical, such as radicals of adonitol, arabitol, dulcitol, erythritol, ethyleneglycol, glycerol, inositol, lactitol, maltitol, mannitol, propyleneglycol, ribitol, sorbitol, threitol and xylitol, and of methanol, ethanol, ethanediol, isopropanol, n-propanol, 1,3-propanediol, and other poly-alcohols.

Even more preferably $R_1$ is selected from the group consisting of radicals of alcohols such as, choline, ethanolamine, ethanol, glycerol, inositol, tyrosine and serine and still more preferably from the alcohol moieties of phosphoglycerides or phosphoglyceride-alcohols, such as choline, serine, ethanolamine, glycerol or inositol.

$R_1$ is most preferably a hydroxyl group.

(A) can have any desired counter-ion for the formation of a salt of a sphingolipid according to the formula (I).

It is possible that the amino group such as may be present in the form of $Q_1$ in a sphingolipid according to the formula (I) is modified, e.g. by single or multiple methylation, alkylation, acylation of acetylation or by modification to a formic acid amide.

Also the free hydroxyl groups in the formula (I), specifically those in $R_3$ may be modified in ways known to the skilled person.

Further, all possible racemates and (dia)stereoisomers of a sphingolipid according to the formula (I) can be used in the present invention. It is possible to use compounds according to the formula (I) wherein $Q_1$ is substituted by e.g. H, a hydroxyl, a carboxyl or a cyano group. Preferred is a compound wherein $Q_1$ is the amino group.

$R_2$ is H or unsaturated or saturated ($C_1$-$C_{30}$) alkyl chain and $R_3$ is unsaturated or saturated ($C_1$-$C_{30}$) alkyl chain.

The term alkyl as used herein refers to a saturated or unsaturated straight chain, branched or cyclic, primary, secondary or tertiary hydrocarbon of $C_1$-$C_{30}$, optionally substituted, and comprises specifically methyl, ethyl, propyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethylbutyl, heptyl, octyl, nonyl, decyl, undecyl, dodecyl, tridecyl, tetradecyl, pentadecyl, hexadecyl, heptadecyl, octadecyl, nonadecyl, eikosyl, heneikosyl and dokosyl and isomers thereof.

The $C_1$-$C_{30}$ alkyl chain or -group may be optionally substituted with one or more groups selected from the collection consisting of hydroxyl, amino, alkylamino, arylamino, alkoxy, aryloxy, nitro, cyano, sulphonic acid, sulphate, sulphonate, phosphonate or phosphate, either unprotected or protected insofar as desired. These substitutes are known to the person skilled in the art, for example from Greene et al., Protective Groups in Organic Synthesis, John Wiley & Sons, $2^{nd}$ Edition, 1991. Preferred embodiments of $C_1$-$C_{30}$ alkyl chains constitute $C_8$-$C_{24}$ alkyl chains.

A compound of the formula (I) is a sphingolipid, or a precursor, a derivative or pharmaceutically acceptable salt thereof.

Even more preferably, in a compound according to the formula (I), or a precursor, a derivative or a pharmaceutically acceptable salt thereof, $R_1$ is a hydroxyl group, t is 0, $R_2$ is hydrogen, $R_3$ is unsaturated or saturated ($C_1$-$C_{30}$) alkyl, $Q_1$-$R_2$ together is an amine group. More preferably therefore, a sphingolipid used in embodiments of the present invention is a sphingolipid with the general formula (II):

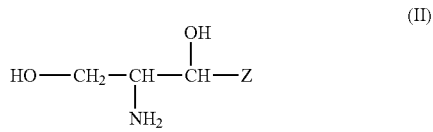

(II)

wherein and Z is $R_3$ or CH(OH)—$R_3$ and $R_3$ is an unsaturated or saturated ($C_1$-$C_{30}$) alkyl chain.

In an even more preferred embodiment of the present invention, a phytosphingosine, sphingosine, sphinganine, ceramide, glycosylceramide and/or sphingomyelin is used, since these compounds show excellent prevention of hepatic fat accumulation in animal models. In a most preferred embodiment of the present invention, a phytosphingosine is used.

Because the simple sphingolipids, i.e. the sphingoid bases, such as e.g. phytosphingosine, sphingosine, and sphinganine, have the same effect as more complex sphingolipids such as ceramide III, sphingomyelin and glycosylceramide, it is preferred to use the simple sphingolipids in aspects of the present invention.

Besides sphingomyelin, phytosphingosine, sphingosine, sphinganine, ceramide and glycosylceramide also derivatives of these compounds may be used in aspects of the present invention. For instance, instead of a hydroxyl headgroup, a choline phosphate, ethanolamine phosphate, serine phosphate, inositol phosphate, glycerol phosphate, glucose or galactose head group may be used as $R_1$ group in a compound according to the formula (I). Basically all headgroups within the definition of R1 above may be used for derivatization of phytosphingosine, sphingosine and sphinganine. A derivative such as lyso-sphingomyelin may also be used in embodiments of the present invention.

It is also possible to use a combination of sphingolipids according to the formula (I) and/or (II) and/or (III) in aspects of the present invention.

In principle, sphingolipids according to the formula (I) and/or (II) and/or (III) of all possible sources are suitable for use in aspects and embodiments of the present invention. For instance, a suitable sphingolipid such as phytosphingosine may be obtained from plants such as corn (Wright et al., Arch. Biochem. Biophys. 415(2), 184-192 and references therein), from animals (skin fibroblasts) or from micro-organisms such as yeasts (such as *Pichia ciferii*). The sphingolipids may be isolated from these organisms or can be used in a less pure form, i.e. as an enriched fraction, or in the case of microorganisms such as yeasts by taking the complete organism(s) or fractions thereof. Further, sphingolipids may be isolated from other suitable sources, such as from milk, egg, soy, yeast, bacteria, algae, plants, meat, brain, etc. or may be chemically or enzymatically prepared, for use in a food item, food supplement and/or pharmaceutical composition according to the invention.

For application in a food item or food supplement according to the present invention a sphingolipid is preferably derived from a food-grade source. Examples of suitable food-grade sources are e.g. bakery yeast, brewers yeast and egg, and certain types of bacteria, (filamentous) fungi, sponges and algae, in particular, but not exclusively those species of bacteria, yeast and fungi which are generally recognized as safe (GRAS). Bacterial sources of sphingolipids are e.g. known from U.S. Pat. No. 6,204,006.

Sphingolipids may be derived from the above sources by methods known to the skilled person for instance by extraction with (organic) solvents, chromatographic separation, precipitation, crystallization and/or enzymatic of chemical hydrolysis. The production of a sphingolipid-enriched (specifically a sphingomyelin-enriched) fraction from milk is for instance known from WO94/18289. Sphingolipids may also be derived from fat concentrates of various animal products such as milk products, egg products and blood products such as known from U.S. Pat. No. 5,677,472.

Methods for the preparation of sphingolipids and sphingolipid derivatives are i.a. known from EP 0 940 409, WO 98/03529, WO 99/50433 and U.S. Pat. No. 6,204,006 and the artisan will be capable of preparing derivatives by these and other methods. Various routes for obtaining sphingosines are described by D. Shapiro in "Chemistry of Sphingolipids", Hermann, Paris (1969). Methods for producing certain phytosphingolipid derivatives are known to the skilled person, for instance it is known from U.S. Pat. No. 6,204,006 and U.S. Pat. No. 5,618,706 to derive tetraacetyl-phytosphingosine (TAPS) from microbial sources (i.e. *Pichia ciferrii*) and to subject this TAPS to hydrolysis to yield phytosphingosine.

A sphingolipid according to the formula (I), or a precursor, a derivative or a pharmaceutically acceptable salt thereof, may also be synthesized by known methods such as e.g. known from U.S. Pat. Nos. 5,232,837 and 5,110,987, or by standard modifications of these methods.

A known issue relating to the administration of sphingolipids, be it in foods or in pharmaceutical compositions, is that they can be metabolized. This is particularly relevant for application of sphingolipids in the digestive tract. This issue may be addressed by administering a sphingolipid according to the formula (I), more preferably according to formula (II) or (III), or a derivative or a pharmaceutically acceptable salt thereof, alone or in combination, as a so-called precursor compound which compound comprises certain substituents as a result of which the compound can no longer, or only at reduced rates, be metabolized. These precursors are preferably resistant to hydrolysis in the upper parts of the digestive tract (e.g. mouth, stomach), and are for instance split relatively easy in the lower part of the digestive tract (e.g. coecum, colon), if the sphingolipid should have its working especially there. Preferably, when the intake of the precursor is via the oral route, the intact or metabolized precursors are taken up into the blood stream and transported to the target organs, especially liver, muscle and adipose tissue where they may be activated in order to exert their beneficial effect. Thus, it is possible that activation occurs when the compound has been absorbed from the digestive tract, e.g. in the blood or the liver. As a result, the amount of the compound is raised at those locations where the sphingolipid has its action. For instance, a sphingolipid precursor may be used that can be split or activated in vivo by a suitable enzyme so that the sphingolipid is liberated that may reduce the levels of cholesterol and triglycerides in the subject. Sphingolipid precursors have been described in WO 99/41266.

It is possible to modify a precursor of a sphingolipid according to the formula (I), (II), (III) or (IV) by an in situ enzymatic or chemical conversion, i.e. in the body, to a sphingolipid according to the formula (I), (II), (III) or (IV), which can be used in embodiments of the present invention. Such precursors of a sphingolipid according to the formula (I), (II), (III) or (IV) are therefore also suited for use according to the invention. A condition is that the precursor is converted in the body, e.g. preferably in the intestine, to a sphingolipid according to the formula (I), (II), (III) or (IV), e.g. by enzymatic conversion, in which case there is in situ activation. It is therefore, for instance possible to administer together with e.g. sphingomyelin, the enzyme sphingomyelin deacylase which may convert the sphingomyelin to lyso-sphingomyelin. Another possibility is to use sphingomyelinase to convert sphingomyelin into ceramide. In its turn ceramide can be broken down by ceramidase into a sphingoid base structure and a fatty acid. Other examples of enzymes may for instance be found in Sueyoshi et al., (Sueyoshi N, Izu H, Ito M. 1997. *J Lipid Res.* 38(9):1923-7). Preferably, however, the sphingolipid according to the formula (I), (II), (III) or (IV) is not used as a precursor but in its "active" form in a food item or a food supplement or a pharmaceutical preparation.

A sphingolipid according to the formula (I), (II), (III) or (IV), or a precursor, a derivative or a pharmaceutically acceptable salt thereof, may be provided to a subject in need thereof for prophylactic or therapeutic reasons. A sphingolipid according to the formula (I), (II), (III) or (IV), or a precursor, a derivative or a pharmaceutically acceptable salt thereof, may be provided to a subject in need thereof in the form of a food item or food supplement, or in the form of a pharmaceutical preparation, all such administration forms being capable of preventing hepatotoxic effects of medicaments, the development and/or to alleviate the severity of hepatic steatosis, fibrosis and cirrhosis. In particular, the development and/or severity of hepatic steatosis is considered.

A sphingolipid according to the formula (I), more preferably according to formula (II), yet more preferably according to formula (III), most preferably phytosphingosine or a precursor, a derivative or a pharmaceutically acceptable salt thereof, may be used in a food item or food supplement. A food supplement is defined as a composition that can be consumed in addition to the normal food intake and which comprises elements or components that are not or in only minor amounts, present in the normal diet and of which sufficient or increased consumption is desired. The composition of a food item does not necessarily differ much from that of a food supplement.

A food item or food supplement as disclosed herein comprises an amount of sphingolipids according to the formula (I), (II), (III) or (IV) that is higher than the amount that would normally or without human intervention occur or be found in said food item or food supplement. This elevated amount of a sphingolipid according to the formula (I), (II), (III) or (IV) may arise through specific addition of said sphingolipid to a food item that does not normally comprise said sphingolipid in said elevated amount, i.e. by enrichment of the food item with said sphingolipid. Alternatively genetic engineering may be used to produce food items comprising said sphingolipid in an elevated amount, for instance by engineering the biosynthetic routes for the production of such sphingolipids in a plant, or yeast or other micro-organism used for the production of a food item in such a way that said sphingolipid is produced in said organism in an elevated amount.

Since amounts of sphingolipids such as phytosphingosine, sphingosine, sphingomyelin, lyso-sphingomyelin or sphinganine may differ considerably between various food items there is no general value for the amount which is said to be an elevated amount or of an enriched food item. In general, milk, which normally contains relatively high amounts of sphingomyelin, is said to comprise an elevated amount at higher absolute concentrations than for instance a potato, which contains no or only minute amounts of sphingomyelin.

A sphingolipid-enriched food item or food supplement as described above may suitably comprise 0.01 to 99.9 wt. % of a sphingolipid according to the formula (I), (II), (III) or (IV). In a preferred embodiment such a food item or food supplement comprises from 0.01 to 50 wt. %, preferably from 0.01 to 10 wt. %, more preferably from 0.01 tot 5 wt. % of a sphingolipid according to the formula (I), (II), (III) or (IV) or derivatives, precursors or acceptable salts thereof.

In order to make a food item or food supplement comprising an elevated amount a sphingolipid according to the formula (I), (II), (III) or (IV) suitable for human or animal consumption, the nutritional value, texture, taste or smell may be improved by adding various compounds to said item or supplement. The skilled person is well aware of the different sources of protein, carbohydrate and fat that may be used in food items or food supplements according to the invention and of the possible sweeteners, vitamins, minerals, electrolytes, coloring agents, odorants, flavoring agents, spices, fillers, emulsifiers, stabilizers, preservatives, anti-oxidants, food fibers, and other components for food items that may be added to improve its nutritional value, taste or texture. The choice for such components is a matter of formulation, design and preference. The amount of such components and substances that can be added is known to the skilled person, wherein the choice may e.g. be guided by recommended daily allowance dosages (RDA dosages) for children and adults and animals.

Portions for intake of the food item or food supplement may vary in size and are not limited to the values corresponding to the recommended dosages. The term "food supplement" is herein not intended to be limited to a specific weight or dosage.

A composition of a food item or food supplement as described above may in principle take any form suited for consumption by man or animal. In one embodiment the composition is in the form of a dry powder that can be suspended, dispersed, emulsified or dissolved in an aqueous liquid such as water, coffee, tea, milk, yogurt, stock or fruit juice and alcoholic drinks. To this end, the powder may be provided in unit-dosage form.

In an alternative preferred embodiment a composition in the form of a dry powder is tabletted. To that end, a composition for a food supplement according to the invention may very suitably be provided with fillers, such as microcrystalline cellulose (MCC) and mannitol, binders such as hydroxypropylcellulose (HPC), and lubricants such as stearic acid or other excipients.

A composition of a food item or food supplement as described above may also be provided in the form of a liquid preparation wherein the solids are suspended, dispersed or emulsified in an aqueous liquid. Such a composition may be admixed directly through a food item or may e.g. be extruded and processed to grains or other shapes.

In an alternative embodiment a food item or food supplement may take the shape of a solid, semi-solid or liquid food item, such as a bread, a bar, a cookie or a sandwich, or as a spread, sauce, butter, margarine, dairy product, and the like. Preferably, a sphingolipid according to the present invention is applied in a dairy product, such as for instance a butter or margarine, custard, yogurt, cheese, spread, drink, or pudding or other dessert. The sphingolipid can also be used in butters or fats used for frying and baking, because they are relatively stable and will not be degraded by high temperatures. This characteristic also enables use of the sphingolipid in food items or food supplements that undergo a pasteurization or sterilization treatment. Diet products also constitute preferred embodiments of food items or food supplements according to the invention.

If a food item according to the invention is used as an animal feed, the food item may e.g. be prepared in the form of a powder, a grain, a waffle, a porridge, a block, a pulp, a paste, a flake, a cook, a suspension or a syrup.

For administering to humans the food item of the invention may very suitably be prepared in the form of a food supplement.

A very suitable food item comprising a sphingolipid in accordance with the present invention would constitute an alcoholic drink, which alcoholic drink would, upon excessive consumption, effectively prevent the development of liver steatosis in the consumer.

The present invention further relates to a method for the preparation of a food item or food supplement according to the invention, comprising enriching a food item or food supplement with a sphingolipid according to the formula (I) and/or (II) and/or (III), or a precursor, a derivative or a pharmaceutically acceptable salt thereof.

In one embodiment the invention provides a method for the preparation of a food item or food supplement enriched with a sphingolipid, comprising processing a sphingolipid according to the formula (I), (II), (III) or (IV), or a precursor, a derivative or a pharmaceutically acceptable salt thereof in a food item or food supplement, preferably to an amount of 0.01 to 99.9 wt. %, more preferably to an amount of from 0.01 to 50 wt. %, even more preferably to an amount of from 0.01 tot 10 wt. %, and most preferably to an amount of from 0.01 tot 5 wt. %. The amount of sphingolipid processed in a food item according to the invention depends on the type of sphingolipid and its use and the skilled person is capable of determining this amount in the context of the present disclosure.

In a method for preparing a food item according to the invention the food item may first be prepared separately and then be joined with a sphingolipid to provide a food item according to the invention wherein said sphingolipid is incorporated in the food item. The food item may be separately prepared by conventional methods such as by mixing, baking, frying, cooking, steaming or poaching and may, if necessary, be cooled prior to joining with the sphingolipid. According to another suitable embodiment, the sphingolipid is incorporated as a component in the food item during the preparation thereof.

A food item or food supplement according to the present invention may very suitably be defined as a nutraceutical composition. Nutraceuticals can be defined as natural products that are used to supplement the diet by increasing the total dietary intake of important nutrients. This definition includes nutritional supplements such as vitamins, minerals, herbal extracts, antioxidants, amino acids, and protein supplements. Nutraceutical products fit into the newly created product category of "Dietary Supplements" as established by the F.D.A. in the Dietary Supplement Act of 1994. This act specifically defined dietary supplements to include: vitamins, minerals, herbs or other botanicals, antioxidants, amino acids, or other dietary substances used to supplement the diet by increasing the total daily intake.

A "nutraceutical composition" is defined herein as a food composition fortified with ingredients capable of producing health benefits. Such a composition in the context of the present invention may also be indicated as foods for special dietary use; medical foods; and dietary supplements. The food item and/or food supplement of the present invention is a nutraceutical composition since it is fortified with one or more sphingolipids according to the invention and since it is capable of treating or preventing hepatotoxicity of medicaments, hepatic steatosis, fibrosis and/or cirrhosis.

The present invention also relates to a method of treatment of subjects suffering from hepatic steatosis, fibrosis and/or cirrhosis said method comprising administering to subjects in need thereof a therapeutically effective amount of a pharmaceutical composition, said composition comprising a sphingolipid according to the formula (I), more preferably according to formula (II), yet more preferably according to the formula (III), most preferably phytosphingosine, sphingosine, sphinganine, glycosylceramide, ceramide, or sphingomyelin or precursors, derivatives or pharmaceutically acceptable salts thereof and a pharmaceutically acceptable carrier, and optionally one or more excipients.

The pharmaceutical composition may also comprise a suitable pharmaceutically acceptable carrier and may be in the form of a capsule, tablet, lozenge, dragee, pill, droplet, suppository, powder, spray, vaccine, ointment, paste, cream, inhalant, patch, aerosol, and the like. As pharmaceutically acceptable carrier, any solvent, diluent or other liquid vehicle, dispersion or suspension aid, surface active agent, isotonic agent, thickening or emulsifying agent, preservative, encapsulating agent, solid binder or lubricant can be used which is most suited for a particular dosage form and which is compatible with the sphingolipid.

A pharmaceutical composition may also contain a pharmaceutically acceptable carrier. The term "pharmaceutically acceptable carrier" refers to a carrier for administration of the therapeutic agent. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

For therapeutic treatment, sphingolipid may be produced as described above and applied to the subject in need thereof. The sphingolipid may be administered to a subject by any suitable route, preferably in the form of a pharmaceutical composition adapted to such a route and in a dosage that is effective for the intended treatment. Therapeutically effective dosages of the sphingolipid required for treating the disorder, for instance for prevention and/or treatment of a disorder selected from the group consisting of hepatic steatosis, fibrosis and/or cirrhosis in the body of a human or animal subject, can easily be determined by the skilled person, for instance by using animal models.

The term "therapeutically effective amount" as used herein refers to an amount of a therapeutic, viz. a sphingolipid according to the present invention, to reduce or prevent hepatotoxicity, hepatic steatosis, fibrosis and cirrhosis, or to exhibit a detectable therapeutic or prophylactic effect. The effect can be detected by, for example, measurement of blood ALAT or ALT, blood sugar, blood serum triglycerides and/or cholesterol as described herein or by any other suitable method of assessing the progress or severity of hepatotoxicity, hepatic steatosis, fibrosis and/or cirrhosis which methods are known per se to the skilled person. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician or experimenter. Specifically, the compositions of the present invention can be used to reduce or prevent hepatotoxicity, hepatic steatosis, fibrosis and/or cirrhosis and/or accompanying biological or physical manifestations. Methods that permit the clinician to establish initial dosages are known in the art. The dosages to be administered must be safe and efficacious.

For purposes of the present invention, an effective daily dose will be from about 0.01 µg/kg to 1 g/kg and preferably from about 0.5 µg/kg to about 400 mg of the sphingolipid/kg body weight in the individual to which it is administered.

Yet in another alternative embodiment, the sphingolipid or compositions of the invention may be administered from a controlled or sustained release matrix inserted in the body of the subject.

Dosages for achieving the therapeutic effects of the medicament, pharmaceutical composition, food item or food supplement described herein may easily be determined by the skilled person. For purposes of the present invention, an effective dose will be from about 0.01-5% of the dry food weight in the individual to which it is administered, meaning that for an adult human being the daily dose will be between about 0.04 and 35 grams of sphingolipid. Highly preferred dosages of sphingolipid in the diet are between 0.1% and 5 wt. % of sphingolipid based on the weight of the dry food, still more preferably between 0.2 wt. % and 1 wt. %.

Preferably a pharmaceutical composition as described above is intended for oral application, and although intravenous or intramuscular administration is also possible, oral administration is preferred. Compositions for oral application will usually comprise an inert diluent or an edible carrier. The compositions may be packed in e.g. gelatin capsules or may be tabletted in the form of tablets. For oral therapeutic application the active compound may be administered with excipients and e.g. used in the form of powders, sachets, tablets, pills, pastilles or capsules. Pharmaceutically acceptable binders and/or adjuvants may also be comprised as constituents of the pharmaceutical composition.

The powders, sachets, tablets, pills, pastilles, capsules and such may comprise each of the following components or compounds of similar import: a filler such as microcrystalline cellulose (MCC) or mannitol; a binder such as hydroxypropylcellulose (HPC), tragacanth gum or gelatin; an excipient such as starch or lactose; a desintegrant such as alginate or corn starch; a lubricant such as magnesium stearate; a sweetener such as sucrose or saccharose; or a flavoring substance such as peppermint or methyl salicylic acid.

When dosing is in the form of a capsule, the capsule may comprise apart from the elements mentioned above a liquid carrier such as an oil. Dosage form may further be provided with coatings of sugar, shellac or other agents. The components of the pharmaceutical composition are preferably chosen such that they do not reduce the desired working of the sphingolipid.

A sphingolipid according to the formula (I), (II), (III) or (IV) or the pharmaceutically acceptable salt thereof may also be administered in the form of e.g. an elixir, a suspension, a syrup, a waffle or a chewing gum.

In a pharmaceutical composition as described above, a sphingolipid according to the formula (I), (II), (III) or (IV), or a precursor, a derivative or a pharmaceutically acceptable salt thereof, is used in an amount of from 0.01 to 99.9% by (dry) weight, preferably from 0.01 to 10 wt. %, and more preferably from 0.01 to 5 wt. %.

A pharmaceutical composition according to the invention is intended for treating or preventing hepatotoxicity, hepatic steatosis, fibrosis and/or cirrhosis in a subject.

The present invention further relates to a method for the preparation of a pharmaceutical composition for the prevention and/or treatment of a disorder selected from the group consisting of hepatotoxic effects of compounds such as alcohol and medicaments, hepatic steatosis, fibrosis and/or cirrhosis in a subject, comprising processing or incorporating a sphingolipid according to the formula (I), (II), (III) or (IV), or a precursor, a derivative or a pharmaceutically acceptable salt thereof, as an active substance, together with a pharmaceutically acceptable carrier in a pharmaceutical composition.

The preparation of a pharmaceutical composition may very suitably occur by mixing all separate ingredients such as fillers, binders, lubricants and optionally other excipients together with a sphingolipid according to the formula (I), (II), (III) or (IV) or a precursor, a derivative or a pharmaceutically acceptable salt thereof, and processing the mixture obtained to a pharmaceutical preparation.

A pharmaceutical composition according to the present invention may, in addition to comprising one or more sphingolipids according to the invention, comprise one or more other pharmaceutically active compounds. Very suitable additional pharmaceutically active compounds are for instance cholesterol-lowering agents such as plant stannols or sterols. A preferred pharmaceutical composition comprising additional pharmaceutically active compounds takes the form of a combined preparation.

The present invention in particular relates to a combined preparation of a sphingolipid as defined hereinabove or a precursor, a derivative or a pharmaceutically acceptable salt thereof and a medicament which is harmful to the liver, or is recognized as hepatotoxic or to cause drug-induced liver toxicity. The advantage of such a combined preparation is that the harm to the liver as imparted by said medicament (i.e. by a pharmaceutical compound or by an excipient comprised in a pharmaceutical composition comprising said compound) is considerably decreased as a result of the presence of the sphingolipid, preferably the presence of the sphingolipid in said preparation. A combined preparation may have the form of at least two separate preparations at least one preparation comprising a sphingolipid and at least another preparation comprising the liver-damaging medicament, which two separate preparations are packaged together and intended for simultaneous, separate or sequential use. Preferably, however, a combined preparation according to the present invention comprises a sphingolipid and a liver-damaging medicament together in the form of a single preparation.

The present invention thus contemplates the prevention or inhibition of drug- or drug excipient induced liver toxicity or liver damage in general terms, preferably arising from, but not limited to the development of steatosis, fibrosis and/or cirrhosis associated with acute or chronic use of drugs. Examples of drugs and excipients that have been associated with liver toxicity are alcohol, paracetamol (acetaminophen), anticonvulsants (for example valproic acid), antifungals (for example azole fungicides), low molecular weight heparins, halothane, vitamin A and derivatives, amiodarone, perhexyline, tamoxifen, steroids, statins and combinations thereof.

Particularly preferred medicaments used in combined preparations with a sphingolipid as defined herein are paracetamol, statins and/or liver damage-causing steroid hormones.

In particular, the present invention contemplates the use of sphingolipids to inhibit or prevent liver-damage which results from hepatotoxic pharmaceutical compounds, by providing such damaging pharmaceutical compounds in combination with a sphingolipid according to the invention. In a particularly preferred embodiment, therefore, the present invention relates to a combined preparation of a sphingolipid as defined hereinabove or a precursor, a derivative or a pharmaceutically acceptable salt thereof, and a medicament which is harmful to the liver, or is recognized as hepatotoxic or to cause drug-induced liver toxicity, for the simultaneous, separate or sequential use in therapy.

In another aspect, the present invention relates to the use of a sphingolipid as defined hereinabove or a precursor, a derivative or a pharmaceutically acceptable salt thereof, and a medicament which is harmful to the liver, or is recognized as hepatotoxic or to cause drug-induced liver toxicity for the manufacture of a combined preparation for simultaneous, separate or sequential use in the prevention of liver disease, preferably hepatic steatosis.

In preferred embodiments of these aspects of combined preparations and their use, the medicament which is harmful to the liver, or is recognized as hepatotoxic or to cause drug-induced liver toxicity is a medicament that causes steatosis, preferably steatosis and/or disorders directly resulting therefrom, such as hepatic fibrosis and/or hepatic cirrhosis.

Almost 1000 pharmaceutical agents are recognized to cause hepatotoxicity, and drug-induced liver toxicity accounts for approximately 15-25% of fulminant hepatic failure cases and nearly 2000 deaths annually in the United States [H. J. Zimmerman, The spectrum of hepatotoxicity, in: Hepatotoxicity: The Adverse Effects of Drugs and other Chemicals on the Liver, second ed., Lippincott Williams & Wilkins, Philadelphia, 1999, pp. 3-11]. Whether a medicament is harmful to the liver may be determined by methods well within reach of the skilled person, see for instance the reference of Zimmerman, supra. For instance, hepatic steatosis, hepatic fibrosis and/or hepatic cirrhosis may be observed during animal trials for testing the efficacy of such medicaments, the observation of which indicates that such medicaments are harmful to the liver. Alternatively, specific markers of liver health may be monitored during administration of the medicament to a subject. For instance, increased plasma levels of the enzyme ALAT in mice or ALT in humans that receive a particular medicament are indicative that the medicament is damaging to the subject's liver. Thus, a use in the prevention and/or inhibition of liver damage, in particular of steatosis and/or disorders directly resulting therefrom, such as hepatic fibrosis and/or hepatic cirrhosis, may also be described as a use in the prevention and/or inhibition of liver-damage such as may be observed through monitoring of liver-enzymes in the blood of subjects, or may be described as a use in the lowering of plasma or serum levels of liver enzymes in particular as resulting form liver damage.

EXAMPLES

Example 1

Forty-five female heterozygous APOE3*Leiden (E3L) mice were fed a high fat and high cholesterol diet for four weeks (week −4 to 0). The mice were housed during the experiment in clean-conventional animal rooms (relative humidity 50-60%, temperature ~21° C., light cycle 6 am to 6 pm). Mice were supplied with food and acidified tap water ad libitum.

At week 0, the mice were randomized on the basis of plasma total triglyceride and cholesterol levels into a control group of fifteen mice and two treatment groups of fifteen mice.

The groups were:
1. high fat, high cholesterol diet only
2. high fat, high cholesterol diet plus 0.7% (w/w) phytosphingosine 3. high fat, 'high' cholesterol diet with a reduced cholesterol content, resulting in about the same plasma cholesterol level as was obtained in group 2.

The treatment was continued for 16 weeks. During the treatment period, tail blood samples were obtained at week 0, 2, 4, 8, 12, and 16 to measure plasma cholesterol and triglyceride levels and to determine plasma lipoprotein composition.

After sixteen weeks, mice were autopsied, liver weight was determined. Body weight and food consumption were determined every four weeks Diets Dietary ingredients were provided by Hope Farms (Woerden, the Netherlands). For group 1 (high cholesterol), the hypercholesterolemic Western-type diet (W-diet) described by Nishina et al (J. Lipid Res. 1990; 31:859) was supplemented with cholesterol (0.5% w/w, final concentration) and with sodium cholate (0.05% w/w, final concentration). This powdered Western-type diet was mixed with 2% agar and freeze-dried as pellets.

The diet for group 2 (treatment group) was prepared by the addition of 0.7% (w/w) phytosphingosine to the same powdered Western-type diet (i.e. also supplemented with cholesterol (0.5% w/w, final concentration) and sodium cholate (0.05% w/w, final concentration)). The supplemented diet mixture was mixed with 2% agar and freeze-dried as pellets.

The diet W for group 3 (low cholesterol) contained 0.1% cholesterol, and 0.05% sodium cholate (w/w, final concentration). This powdered Western-type diet was mixed with 2% agar and freeze-dried as pellets.

The diets were prepared every eight weeks, and stored in the dark at −20° C. Food was given ad libitum.

Plasma Analysis

Total cholesterol was measured using the kit Chol R1 from Roche. Total triglycerides were measured using the kit Triglycerides GPO-PAP from Roche. ALAT was measured by dry chemistry on a Reflotron (Roche).

Results

Results are displayed in Tables 1-3.

TABLE 1

Final mean body weight (gram) in the experimental groups of mice of Example 1 at week 16 of the experiment

|  | group 1 | group 2 | group 3 |
|---|---|---|---|
| mean | 22.9 | 22.1 | 23.3 |
| sd | 1.0 | 0.8 | 1.5 |

TABLE 2

Final mean liver weight (gram) in the experimental groups of mice of Example 1 at week 16 of the experiment

|  | group 1 | group 2 | group 3 |
|---|---|---|---|
| mean | 1.79 | 1.34 | 1.42 |
| sd | 0.19 | 0.13 | 0.17 |

TABLE 3

Final mean plasma ALAT values (U/L) in the experimental groups of mice of Example 1 at week 16 of the experiment

|  | group 1 | group 2 | group 3 |
|---|---|---|---|
| mean | 213 | 82 | 113 |
| sd | 53 | 46 | 56 |

The differences in liver weight (Table 1) were statistically significant (parametric ANOVA: F=28.86, p<0.0001). The liver weights in both the phytosphingosine-fed group 2 and in the low cholesterol group 3 were significantly lower than in the high cholesterol group 1 (all p<0.001). Body weight (Table 2) and food intake did not differ between the three groups.

The differences in ALAT (Table 3) were statistically significant (parametric ANOVA: F=24.30, p<0.0001). The ALAT values in both the phytosphingosine-fed group 2 and in the low cholesterol group 3 were significantly lower than in the high cholesterol group (all p<0.001).

Example 2

The experiment as described in example 1 was repeated several times but using 1% phytosphingosine as a supplement to the W-diet. Each time, one group (control group, consisting of 6 or 12 apoE3*-Leiden mice) was fed the high fat high cholesterol W-diet. Another group (treatment group, consisting of 6 or 12 apoE3*-Leiden mice), was fed the same high fat high cholesterol W-diet diet supplemented with 1% phytosphingosine.

In all mice the following parameters were determined (after 4 hours of fasting) after a diet period of 4 weeks: plasma total cholesterol (PTC), plasma triglycerides (PTG), plasma free fatty acids (PFFA), liver total cholesterol (LTC), liver triglycerides (LTG), liver cholesteryl esters (LCE), serum amyloid A (SAA) (mg/ml), fibrinogen (in mg/ml), body weight (in g), liver weight (in g), heart weight (in g), ALAT (in U/L). The results showed marked differences in liver structure, chemical composition and function between the control group and the treatment group (see FIGS. 1-2), and marked differences in plasma parameters.

It was found that mice treated with 1% phytosphingosine had significantly lower levels of serum amyloid A (SAA), an inflammatory protein synthetized in the liver, while the plasma level of fibrinogen, another protein synthetized by the liver, was increased, indicative of improved liver function. Plasma lipid levels (total cholesterol, triglycerides and free fatty acids) were all significantly decreased in the 1% PS group.

Liver lipid levels were significantly decreased by treatment of mice with 1% PS in diet W. ALAT (alanine aminotransferase, the mouse equivalent of ALT in humans) was also significantly lowered by treatment with 1% PS in the diet.

A more extensive description of the materials and methods and results of Example 2 is provided now.

Materials and Methods

Sphingolipids: The three sphingolipids that represent the most abundant natural complex sphingolipid classes and the three of the simplest natural sphingolipids, the sphingoid bases that can be formed by enzymatic breakdown of complex sphingolipids in the intestine were used. Sphingomyelin (mainly N-palmitoyl-sphingosine-1-phosphocholine) from egg was obtained from Larodan Fine Chemicals (Stockholm, Sweden). Yeast-derived (semi)synthetic ceramide III (N-stearoyl-phytosphingosine), cerebroside (N-stearoyl-phytosphingosine-1-glucose) and phytosphingosine (PS) were from Cosmoferm BV (Delft, the Netherlands). Sphinganine and sphingosine were from Avanti Polar Lipids (Albaster, Ala.). Animals and diets: Heterozygous female APOE*3Leiden transgenic mice (Van Vlijmen et al. 1994. J. Clin. Invest 93:1403-1410.) (6 months old) were fed a Western-type diet (Hope Farms, Woerden, the Netherlands) containing 15% cocoa butter, 0.25% cholesterol, 1% corn oil, 40.5% sucrose, 20% acid casein, 10% corn starch and 5.95% cellulose (all w/w) for 5 weeks. The mice were allowed free access to food and water. Body weight and food intake were monitored weekly. In the first experiment (FIG. 2), the mice were randomized after these 5 weeks into 7 groups (n=6), based on plasma cholesterol, triglycerides, and body weight. Subsequently, the mice were fed for three weeks the same diet without or with 0.1% (w/w) phytosphingosine (PS), sphingosine, sphinganine, cerebroside, ceramide III, or sphingomyelin. Then, the sphingolipid dose was increased to 0.2% (w/w) for 3 weeks and finally to 0.4% (w/w) for 3 weeks. At randomization, and at 3, 6, and 9 weeks, tail vein blood samples were obtained after a 4 h-fast. In all subsequent experiments, female APOE*3Leiden transgenic mice (6 months old) were fed the Western-type diet for 5 weeks, and randomized as described. Subsequently, they were fed the Western-type diet for 5 weeks, or this diet supplemented with 1.0% (w/w) of PS, before being subjected to experimentation.

Plasma parameters: Tail blood samples were collected in EDTA-coated cups, or in paraoxon-coated capillaries to prevent lipolysis as described in Zambon et al. 1993 (Zambon et al. 1993. *J. Lipid Res.* 34:1021-1028). Plasma lipid parameters were determined using commercial kits for total cholesterol (C) Chol R1 from Roche Diagnostics, Mannheim, Germany), non-esterified free fatty acids (FFA) (NEFA-C; Wako chemicals, Neuss, Germany), Total triglycerides (TG) (Triglyceride GPO-Trinder; Sigma, St. Louis, Mo.), β-hydroxybutyrate (β-HB; Sigma) and ALAT (Reflotron GPT; Roche). Serum amyloid A (SAA) was measured by ELISA (Biosource, Nivelles, Belgium) and fibrinogen by sandwich ELISA, as described in Koopman et al., 2005 (Koopman et al. 2005. Fibrinol Proteol 11:19). For lipoproteins fractionation, groupwise-pooled plasma was size-fractionated by fast protein liquid chromatography (FPLC) on a Superose 6 column (Äkta; Amersham Pharmacia Biotech, Uppsala, Sweden). Fractions were assayed for total C and TG as described.

Hepatic VLDL-TG production: The rate of hepatic VLDL-TG production, de novo apoB secretion, and VLDL composition were determined in overnight-fasted mice. Mice were anaesthetized with vetranquil/fentanyl/midazolam i.p., and injected i.v. with 0.1 ml PBS containing 100 μCi Tran$^{35}$S-label™ (ICN Biomedicals, Irvine, Calif.) to measure the de novo apoB synthesis. After 30 min, the animals received a Triton WR1339 injection (Tyloxapol, Sigma; 500 mg/kg body weight in 100 μl saline) to prevent systemic lipolysis of newly-secreted hepatic VLDL-TG (Aalto-Setala et al. 1992. J. Clin. Invest 90:1889-1900.27) Blood samples were drawn at 0, 15, 30, 60, and 90 min after Triton WR1339 injection and plasma TG concentrations were determined. After 90 min, the animals were sacrificed and blood was collected by retro-orbital bleeding for isolation of VLDL.

VLDL composition: VLDL particles (d<1.019) were separated from other lipoproteins in plasma by density gradient ultra-centrifugation, as described in Jong et al., 1996 (Jong et al. 1996. *Arterioscler. Thromb. Vasc. Biol.* 16:934-940). Protein content of the VLDL fraction was determined by Lowry's assay (Lowry et al., 1951. J. Biol. Chem. 193:265-275), and TG and total C were determined as described above. Phospholipids and free cholesterol were determined using standard commercial kits (Wako Chemicals, Neuss, Germany). The $^{35}$S-apoB content of VLDL was measured after selective precipitation of apoB with isopropanol as described elsewhere (Li et al. 1996 J. Lipid Res. 37:210-220; Pietzsch et al. 1995. Biochim. Biophys. Acta 1254:77-88).

In vivo clearance of VLDL-like TG-rich particles: To determine whether 1% PS accelerates the clearance of TG-rich lipoproteins from plasma, we used radiolabeled emulsion particles as a tool. VLDL-like emulsion particles containing 200 μCi of [$^3$H]triolein and 20 μCi of [$^{14}$C]cholesteryl oleate were prepared and characterized as described in Rensen et al. 1997 (Rensen et al., 1997. J. Lipid Res. 38:1070-1084). Fed mice were anaesthetized as described above and laparotomy was performed. Emulsion particles were injected into the vena cava inferior at a dose of 300 μg TG per mouse. At 2, 5, 10, 20, and 30 min, blood samples (50 μL) were taken from the vena cava inferior and liver samples were tied off, excised, and weighed. $^3$H and $^{14}$C-activities were counted in 10 μl of serum, and corrected for total serum volume (ml) calculated as 0.04706*body weight (g) (Jong et al., supra). After taking the last liver and blood sample, the remainder of the liver, heart, spleen, hind limb muscle, and gonadal, perirenal and intestinal white adipose tissues were harvested. Lipids were extracted overnight at 60° C. in 500 μL of Solvable™, and radioactivity was counted as described in Rensen et al., 1997 (supra).

RNA isolation and RT-PCR: Livers from 4 h-fasted mice fed 1% PS-containing diet or control Western-type diet for 5 weeks were removed immediately after sacrifice, flushed with cold 0.9% NaCl and snap frozen in liquid nitrogen. Total RNA was isolated as described by Chomczynski and Sacchi (Chomczynski, P. and Sacchi, N. 1987. Anal. Biochem. 162: 156-159) by use of RNA-Bee™ (Campro Scientific, Berlin, Germany). cDNA synthesis was performed according to Bloks et al (Bloks et al., 2001. J. Lipid Res. 42:41-50). Real-time quantitative PCR (Heid et al., 1996. Genome Res. 6:986-994.) was performed using an Applied Biosystems 7700 Sequence detector. Primers were obtained from Invitrogen (Paisley, UK) and fluorogenic probes, labelled with 6-carboxyfluorescein (6-FAM), and 6-carboxytetramethylrhodamine (6-TAMRA), were made by Eurogentec (Seraing, Belgium). Primers and probes used were described earlier (Post et al., 2004. Arterioscler. Thromb. Vasc. Biol. 24:768-774.; Heijboer et al., 2005. J. Lipid Res. 46:582-588; Bandsma et al., 2004. J. Biol. Chem. 279:8930-8937). All expression data were subsequently standardized for hypoxanthine guanine phosphoribosyl transferase (HPRT) mRNA levels.

Liver lipid levels: Liver samples taken from 4 h-fasted mice fed 1% PS-containing or control Western-type diet for 5 weeks were homogenized in phosphate-buffered saline (PBS) (10% wet wt/vol) and samples were taken to measure protein content by Lowry's assay. Lipid content was determined by extraction of lipids using the Bligh and Dyer method (Bligh and Dyer. 1959. Can. J. Biochem. Physiol 37:911-917), followed by lipid separation using high performance thin layer chromatography (HPTLC) on silica gel plates as described (Havekes et al. 1987. Biochem. J. 247: 739-746) and analysis by TINA2.09 software (41) (Raytest Isotopen Meβgeräte, Straubenhardt, Germany).

Liver histology: Livers from 4 h-fasted mice fed 1% PS or control Western-type diet for 5 weeks were isolated, fixed in 10% formalin and paraffin-embedded. Liver sections were stained with hematoxylin-phloxine-saffron (HPS) for morphological analysis.

Statistics: The Mann-Whitney U-test was used to determine differences in responses during the intervention period between the control group and the other treatment groups. The criterion for significance was set at p<0.05. All data are presented as mean±SD. Statistical analyses were performed using SPSS11.0 (SPSS, Chicago, Ill.).

Results

Sphingolipids Lower Plasma C and TG in APOE*3Leiden Mice.

Figure 5:
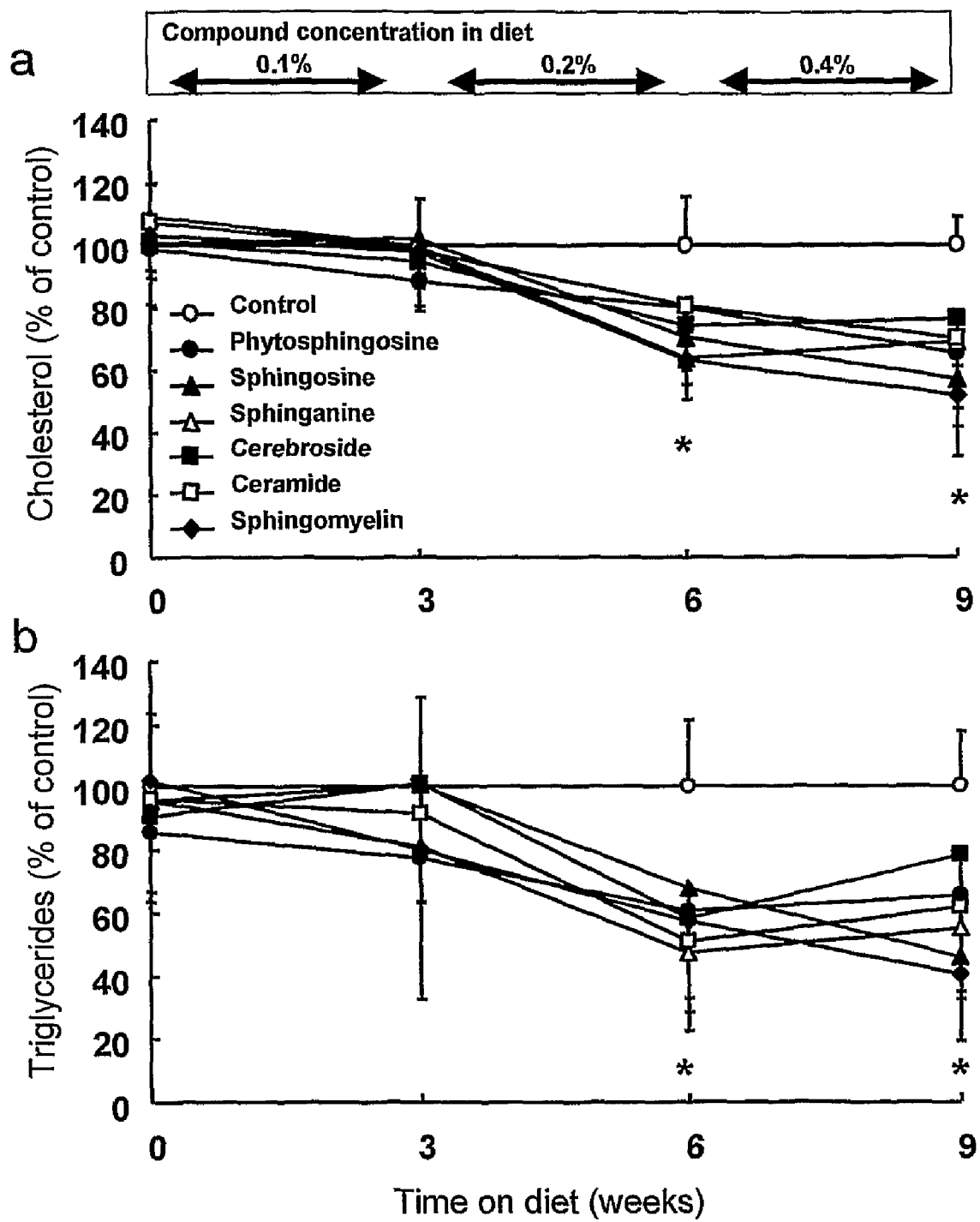
FIG. 5 shows the effect of sphingolipids on plasma cholesterol (C) and TG levels in APOE*3Leiden mice as described in Example 2.

For our initial experiment to evaluate the effect of sphingolipids on plasma C and TG levels in APOE*3Leiden mice we used three simple and three complex sphingolipids (simple: phytosphingosine, sphingosine, and sphinganine; complex: ceramide III, sphingomyelin and cerebroside). At 0.1% of those sphingolipids in the diet no significant effect on plasma C and TG was seen (FIG. 5). At a dose of 0.2% (w/w), all tested sphingolipids significantly decreased plasma levels by 20-40% (FIG. 5). At 0.4%, plasma C was decreased even more by sphingosine, phytosphingosine, ceramide and sphingomyelin. The decrease in TG was about 40% for all sphingolipids at dietary sphingolipid concentrations of 0.2% and 0.4% (FIG. 5B). No differences in food intake or body weight were observed throughout the experiment in mice fed sphingolipids compared to control animals (data not shown). Remarkably, the simplest sphingolipids, the sphingoid bases, have the same potent C and TG lowering effect as their complex sphingolipid derivatives.

Figure 6:
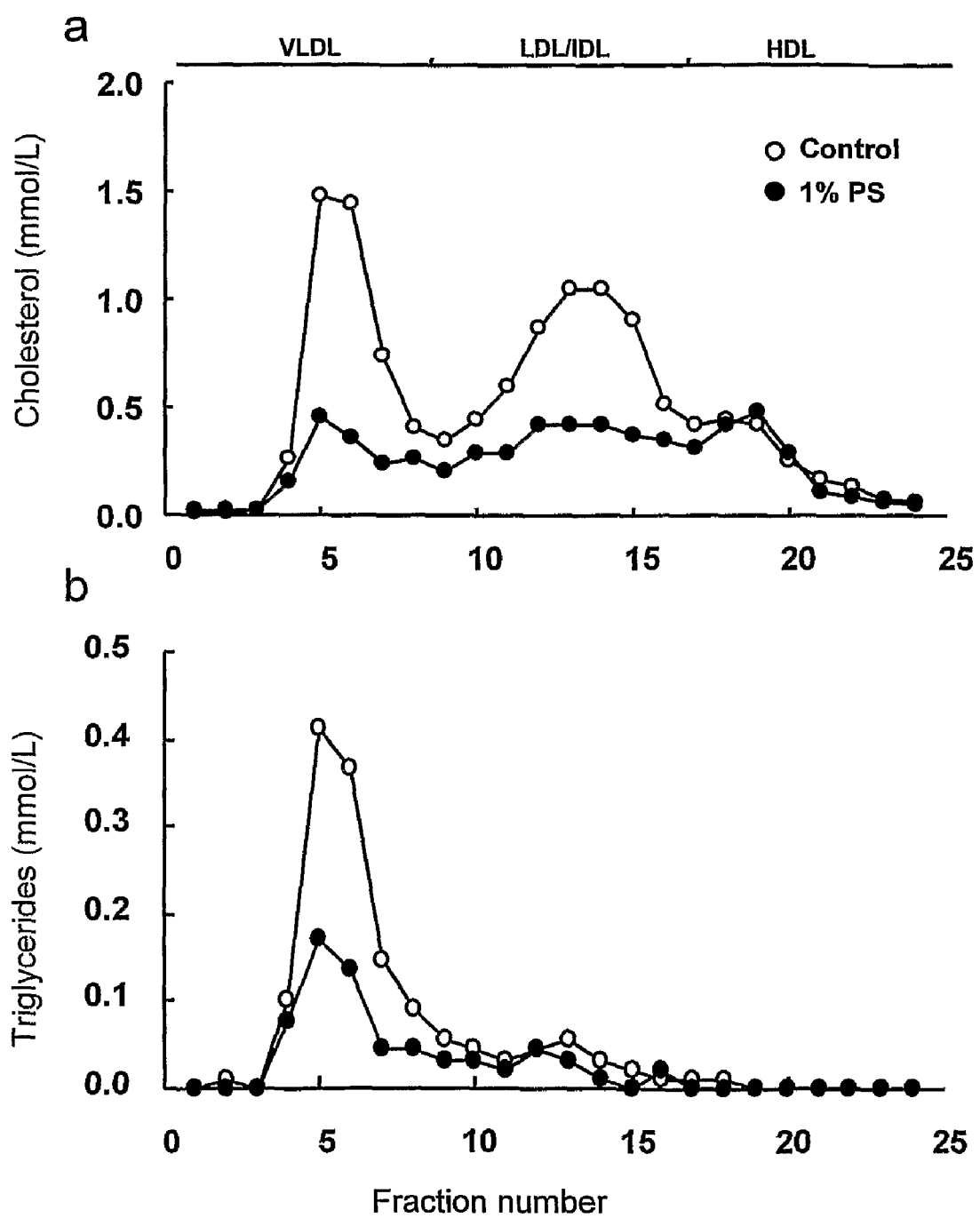
FIG. 6 shows Cholesterol (A) and triglycerides (B) profiles after FPLC separation of plasma lipoproteins. Pooled plasma of 4 h-fasted APOE*3Leiden mice fed a control Western-type diet (open circles) or this diet supplemented with 1% (w/w) PS (closed circles) for 5 weeks was used. After separation, cholesterol and triglycerides were determined in the individual fractions. Data shown are typical of all FPLC separations performed after the use of these diets (see Example 2).
Figure 7:
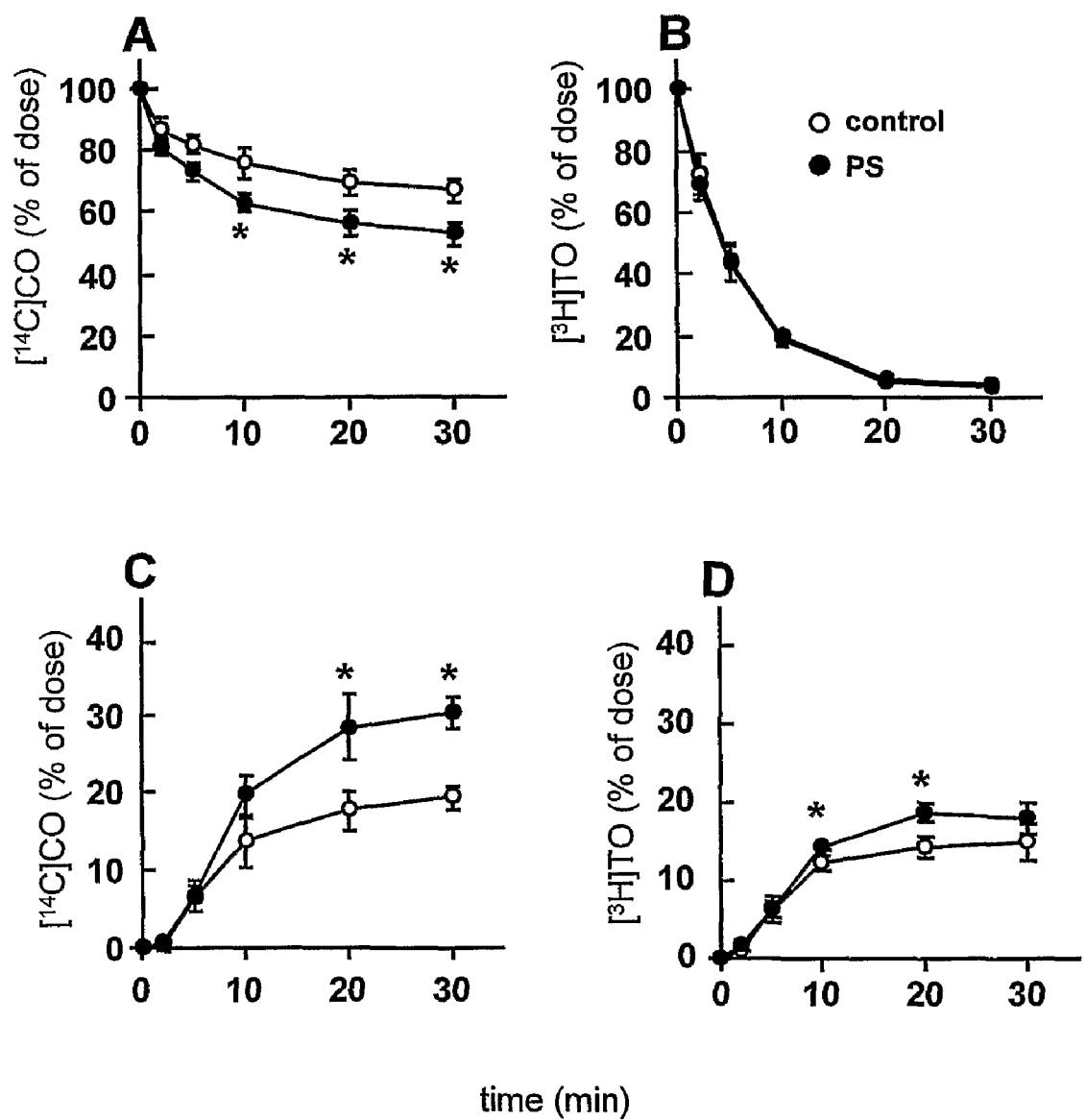
FIG. 7 shows the in vivo clearance of VLDL-like emulsion particles. After 5 weeks of 1% PS-containing (closed circles) or control (open circles) Western-type diet, fed mice were injected with VLDL-like emulsion particles containing [$^3$H]triolein and [$^{14}$C]cholesteryl oleate. Over time, plasma (A,B) and liver (C,D) samples were taken to determine radioactivity. Data shown are mean±SD. *$p<0.05$.

To study the mechanisms underlying the C and TG lowering, we performed studies in mice fed the Western-type diet with or without 1% (w/w) PS for five weeks. This sphingolipid was chosen for all subsequent studies because this sphingolipid is one of the simplest in the sphingolipid class; it is the central structural element of ubiquitous sphingolipids of plants and yeasts that are part of our diet; and this lipid may be formed in situ in the intestine by enzymatic degradation of complex sphingolipids. No effects on body weight or food intake were ever observed (data not shown). As can be seen in Table 4, mice on a 1% PS diet showed, as expected, a strong and significant decrease in plasma C and TG (both p<0.01). Plasma FFA levels were strongly and significantly decreased as well, while plasma β-hydroxybutyrate (a liver-derived ketone body) did not change significantly (Table 4). Plasma pooled groupwise was used to determine lipoprotein profiles of these mice. The lipoprotein profiles showed that the decrease in C and TG was confined to the VLDL and IDL/LDL fractions, while HDL cholesterol did not change (FIG. 6).

TABLE 4

Plasma parameters in 4 h-fasted APOE*3Leiden mice fed a control Western-type diet or a 1% PS-containing Western-type diet for 5 weeks

|  | Control | 1% PS | % Δ |
|---|---|---|---|
| Body weight (g) | 22.2 ± 0.6 | 22.6 ± 1.0 | n.s. |
| Liver weight (g) | 1.34 ± 0.12 | 1.05 ± 0.08 | −22 |
| Total cholesterol (mmol/l) | 14.0 ± 1.2 | 6.1 ± 1.1** | −57 |
| Triglycerides (mmol/l) | 2.80 ± 0.52 | 1.19 ± 0.39** | −58 |
| Free fatty acids (mmol/l) | 1.67 ± 0.31 | 1.06 ± 0.14** | −36 |
| β-hydroxybutyrate (mmol/l) | 0.40 ± 0.25 | 0.49 ± 0.39 | n.s. |

Values shown are means ± SD of 6 mice per group.
**P < 0.01 vs. control.
n.s., not significant.

Phytosphingosine Increases Hepatic VLDL-TG Production

Hepatic VLDL-TG production was studied in overnight-fasted mice using the Triton WR1339 method, and measuring plasma TG accumulation in an acute experiment. In these experiments, mice fed 1% PS-containing diet showed a faster increase of plasma TG levels than the mice fed the control Western-type diet. The VLDL-TG production rate, as determined from the slope of the curves, was increased by 20% (p<0.05) in mice fed PS compared to control mice (Table 5). Analysis of the composition of the VLDL particles (isolated by ultracentrifugation) revealed that the TG content as well as the phospholipid content was increased by 66% and 17%, respectively (p<0.05) in VLDL particles derived from PS-fed mice (Table 5). Total C was, in contrast, decreased by 51% in the VLDL particles from the PS-fed mice (p<0.05). The de novo total apoB production rate in newly synthesized VLDL particles did not differ between mice fed PS-containing diet and control mice (Table 5). The data indicate that the number of VLDL particles secreted by the liver is not affected, but that the VLDL particles contain less C, but more TG in PS treated mice.

TABLE 5

Production rates of VLDL-TG and VLDL-apoB, and VLDL particle composition, of APOE*3Leiden mice fed control or 1% PS-containing Western-type diet for 5 weeks

|  | Control | 1% PS | % Δ |
|---|---|---|---|
| Production rates | | | |
| VLDL-TG production rate (μmol TG/h) | 3.01 ± 0.44 | 3.63 ± 0.52* | +20 |
| apoB production rate (×10$^4$ dpm/ml/h) | 12.80 ± 2.57 | 13.47 ± 2.45 | n.s. |
| VLDL particle composition | | | |
| Total cholesterol (μmol/mg VLDL protein) | 24.39 ± 3.73 | 11.94 ± 2.16*** | −51 |
| Triglycerides (μmol/mg VLDL protein) | 22.28 ± 2.37 | 36.93 ± 7.17*** | +66 |
| Phospholipid (μmol/mg VLDL protein) | 6.47 ± 0.92 | 7.57 ± 1.13* | +17 |

Mice were fasted overnight and injected with $^{35}$S label and Triton WR1339. Timed blood samples were taken to determine triglyceride (TG) levels. At 4 h, VLDL (d < 1.006 g/ml) was isolated by ultracentrifugation, and TG, total cholesterol, phospholipid and protein content were determined.
Values represent means ± SD for 10 mice per group.
*p < 0.05,
***p < 0.001,
n.s. not significant.

Phytosphingosine Increases Liver-Mediated Clearance of Plasma C but not Plasma TG Plasma C and TG levels are not only determined by their production rates, but also by clearance, i.e. by their uptake and/or lipolysis. VLDL-like particles containing [$^3$H]triolein and [$^{14}$C]cholesteryl oleate, which have previously been shown to mimic the metabolic behaviour of TG-rich lipoproteins (Rensen et al., 1997, supra; Rensen et al. 2000. J. Biol. Chem. 275:8564-8571) were used to determine the effects of a 1% PS-containing Western-type diet on plasma clearance. PS accelerated the plasma clearance of [$^{14}$C]cholesteryl oleate ($t_{1/2}$ 39.5±5.3 vs. 74.5±9.9 min for PS-treated vs. control mice, respectively; p<0.05; FIG. 6A). The enhanced removal of C from the blood is corroborated by the increased liver uptake of [$^{14}$C]cholesteryl oleate (+60% at 20 min; p<0.05; FIG. 6B). Although LPL-dependent serum clearance of [$^3$H] TG was not affected ($t_{1/2}$ 4.7±0.3 vs. 4.9±0.3 min for PS-treated vs. control mice; FIG. 6C), the [$^3$H]TG uptake in the liver at 10 min and 20 min after injection was increased significantly in PS-fed mice (FIG. 6D). No effects were observed on the uptake of [$^{14}$C]cholesteryl oleate or [$^3$H]TG-derived radioactivity by various peripheral muscle and adipose tissues (data not shown). Taken together, the results of this experiment indicate an increase in VLDL particle remnant uptake in the liver.

Hepatic mRNA Levels Indicate Increased Lipid Synthesis

Hepatic expression of several genes was studied (Table 6) using RT-PCR on liver samples of 4 h-fasted mice given the 1% PS-containing or the control Western-type diet for 5 weeks. The mRNA levels of genes involved in FA/TG synthesis and secretion (srebp1c, fas, mttp and dgat2) were increased. Apob, dgat1, acc1 and aco transcription levels were unaltered. Furthermore, mRNA levels of C homeostasis genes, like ldlr, srebp2 and hmgcoAred, were also increased. In strong contrast, the two genes involved in bile salt formation studied were decreased (cyp7α and lxrβ), while fxr expression was increased. pparα, pparγ and abca1 expression was not changed (Table 6). Overall, these changes suggest increased hepatic lipid and C synthesis and decreased bile formation. This indicates a shift in hepatic TG and C homeostasis compared to the control situation.

TABLE 6

Hepatic mRNA expression levels (normalized to HPRT) of APOE*3Leiden mice fed a control or a 1% PS-containing Western-type diet for 5 weeks, as determined by RT-PCR

| mRNA of | Control | 1% PS | Change |
|---|---|---|---|
| Lipid homeostasis | | | |
| srebp1c | 100 ± 7% | 194 ± 3%** | ↑ |
| fas | 100 ± 6% | 237 ± 33%* | ↑ |
| acc1 | 100 ± 6% | 138 ± 29% | n.s. |
| mttp | 100 ± 4% | 167 ± 5%** | ↑ |
| dgat1 | 100 ± 25% | 112 ± 27% | n.s. |
| dgat2 | 100 ± 17% | 185 ± 23%* | ↑ |
| aco | 100 ± 12% | 56 ± 9% | n.s. |
| ldlr | 100 ± 7% | 209 ± 14%** | ↑ |
| apob | 100 ± 15% | 105 ± 25% | n.s. |
| Cholesterol homeostasis | | | |
| srebp2 | 100 ± 9% | 317 ± 33%* | ↑ |
| pparα | 100 ± 1% | 125 ± 10% | n.s. |
| pparγ | 100 ± 7% | 119 ± 10% | n.s. |
| lxrα | 100 ± 4% | 162 ± 13%* | ↑ |
| lxrβ | 100 ± 18% | 16 ± 8%* | ↓ |
| fxr | 100 ± 15% | 164 ± 58%* | ↑ |
| hmgcoAred | 100 ± 7% | 444 ± 71%** | ↑ |
| cyp7α | 100 ± 10% | 7 ± 2%* | ↓ |
| abca1 | 100 ± 12% | 79 ± 6% | n.s. |

Values represent means ± SD of 5 mice per group.
*p < 0.05,
**p < 0.01 vs controls.
n.s., not significant;
↑, (upregulated);
↓, (downregulated).

Phytosphingosine Protects Livers from Steatosis

Figure 2A:
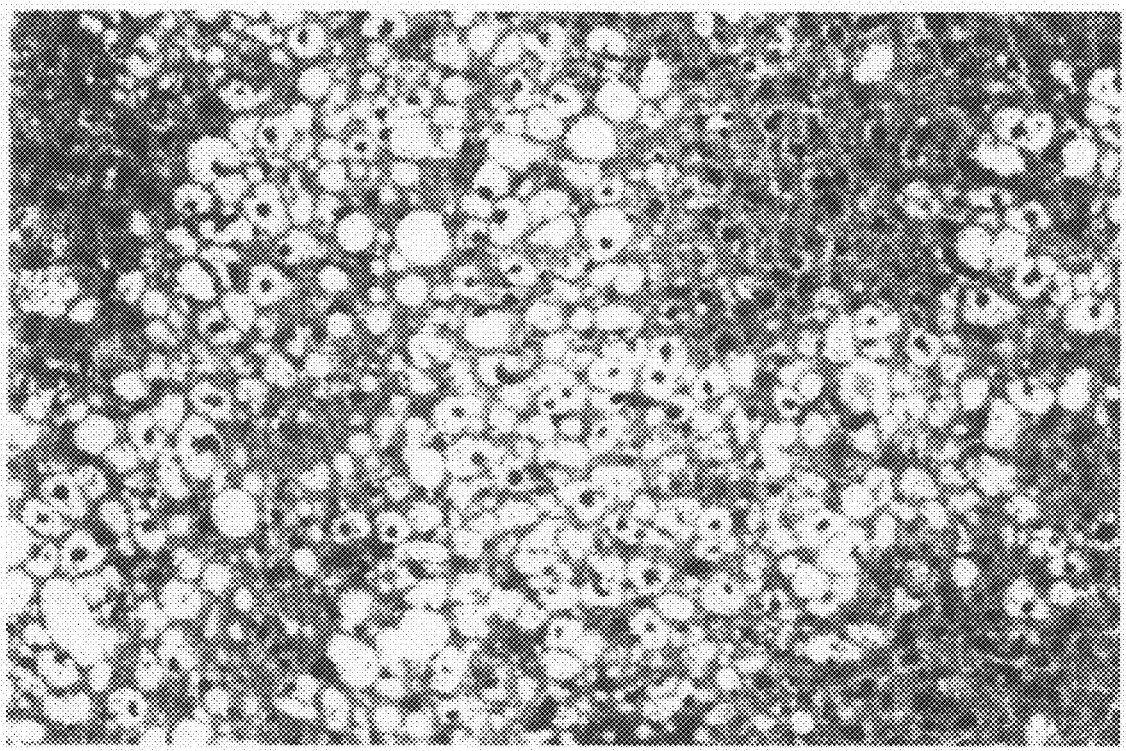
FIG. 2 shows microscopic images (haematoxylin-phloxin-saffron-stained paraffin sections) of the fat deposits in the liver cells of a control-group animal fed a high fat high cholesterol diet (A).
FIG. 2B shows the absence of such fat deposits in the liver of an animal from the group fed the same diet supplemented with 1% phytosphingosine, as described in Example 2.
Figure 2B:
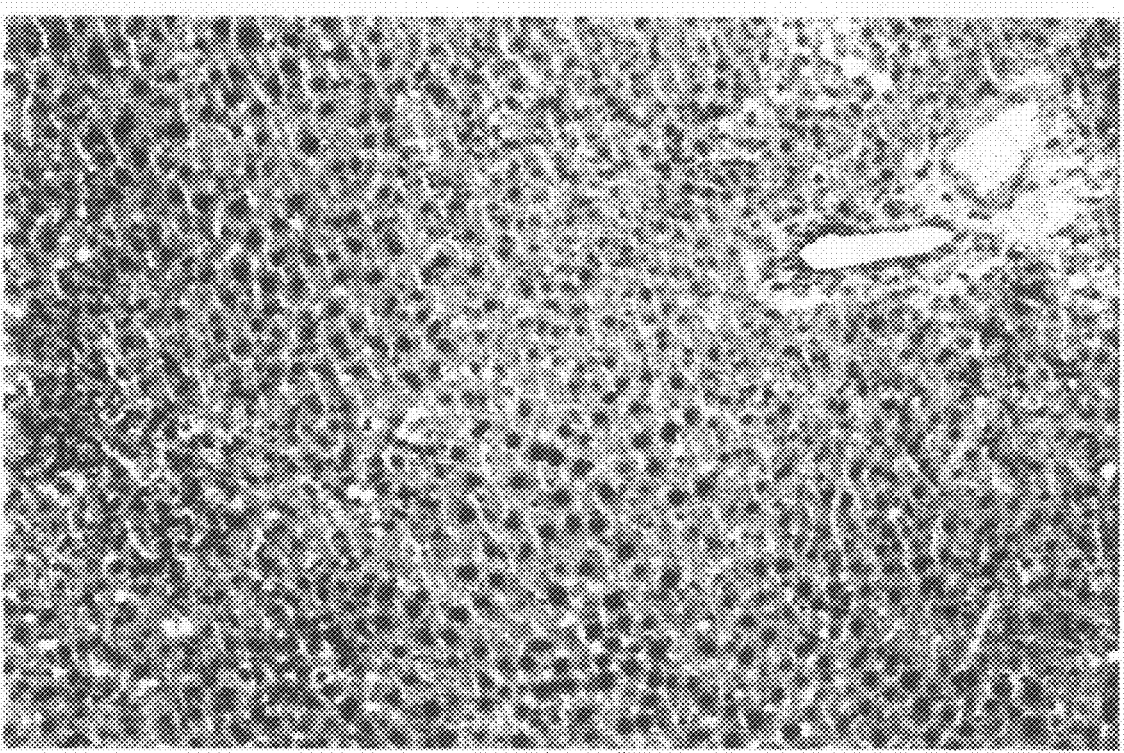
Figure 3:
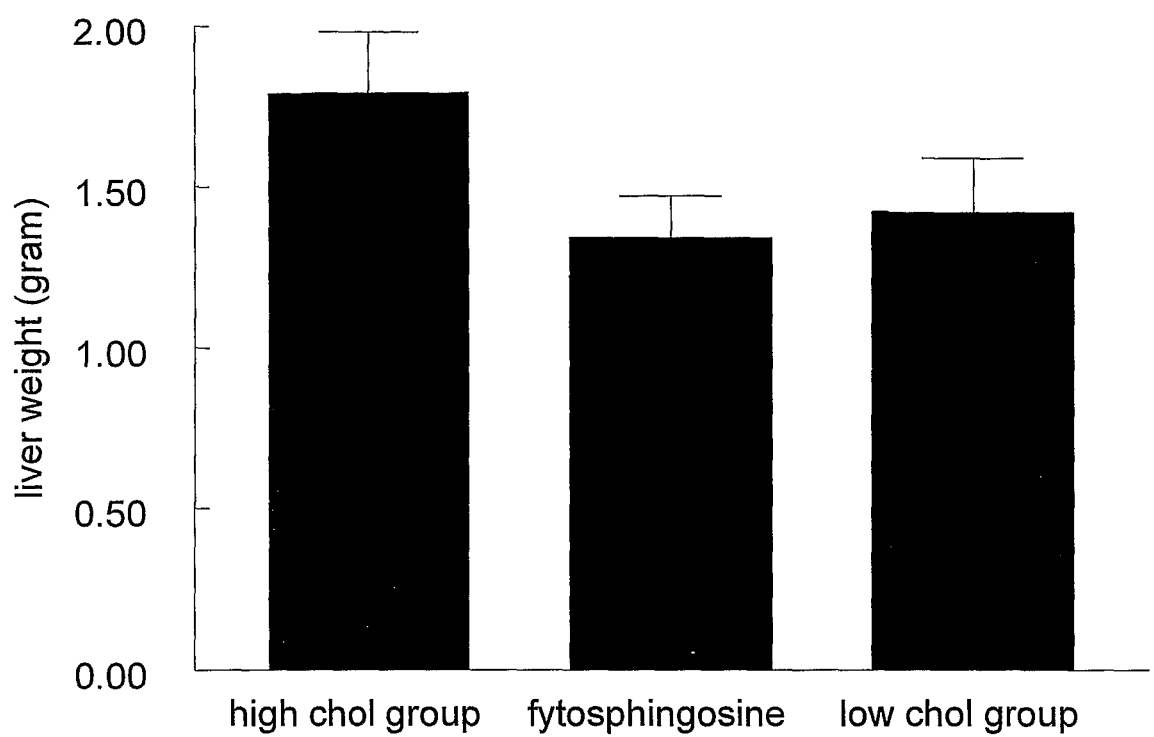
FIG. 3 shows the liver weight of the mice after completion of the experiments as described in Example 1.
Figure 4:
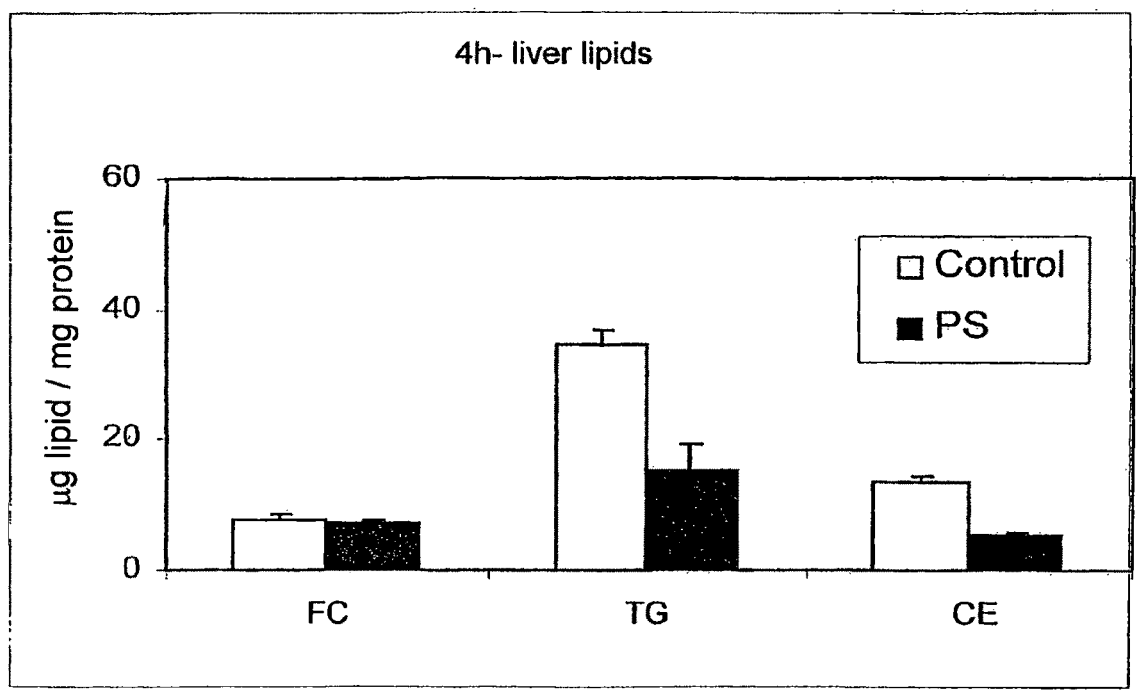
FIG. 4 shows the amount of lipids (FC, (liver) free cholesterol; TG, (liver) triglycerides; CE, (liver) cholesteryl ester) in livers of mice fed during 4 weeks with diet W (control) or diet W supplemented with 1% phytosphingosine (PS) after 4 hours of fast, as described in Example 2.

Increased remnant uptake and increased mRNA expression of genes involved in FA/TG synthesis suggested that intrahepatic TG and C levels are increased in our setting. However, at autopsy of these mice, it was noted that the livers of the mice fed the 1% PS-containing Western-type diet were of normal size, and had a dark-red appearance, whereas the livers of the control mice fed the Western-type diet without PS were enlarged and yellowish (FIG. 1). This indicates that PS fed mice had a decreased hepatic lipid content as compared to control mice. Microscopical examination of HPS-staining sections showed that, compared to controls, PS-fed mice had less lipid-filled vacuoles in the liver cells (FIG. 2). The livers of PS-fed mice weighed significantly less (−22%, p<0.05) than those of the control mice (Table 7). Lipid analysis revealed that livers of PS-fed mice contained less TG (−56%; p<0.05) than control mice. Furthermore, liver cholesteryl esters were decreased by 61% (p<0.05) as was Free C by 11% (p<0.05) in PS-fed mice.

Phytosphingosine Lowers Plasma Inflammatory Markers

Hepatic steatosis is often associated with liver inflammation. We determined plasma ALAT levels, as a measure for liver damage. ALAT levels were decreased by 79% (p<0.05) upon PS feeding. A 74% (p<0.05) decrease in levels of the acute phase marker SAA was found in PS-fed mice. Fibrinogen levels were increased by 42% (p<0.05) in PS-treated mice compared to controls (Table 7)

TABLE 7

Liver lipid parameters and plasma inflammation markers determined in 4 h-fasted APOE*3Leiden mice after feeding a control or a 1% PS-containing Western-type diet for 5 weeks

| | Control | 1% PS | % Δ |
|---|---|---|---|
| Liver parameters | | | |
| Liver weight (g) | 1.34 ± 0.12 | 1.05 ± 0.08** | −22 |
| Triglycerides (μg/mg protein) | 34.62 ± 2.23 | 15.28 ± 3.84** | −56 |
| Free cholesterol (μg/mg protein) | 7.81 ± 0.51 | 6.95 ± 0.78* | −11 |
| Cholesteryl ester (μg/mg protein) | 13.44 ± 0.79 | 5.20 ± 0.79** | −61 |
| Plasma inflammation markers | | | |
| ALAT (U/l) | 189 ± 49 | 41 ± 21** | −79 |
| SAA (mg/ml) | 11.2 ± 3.6 | 3.0 ± 0.3* | −74 |
| Fibrinogen (mg/ml) | 1.6 ± 0.5 | 2.3 ± 0.7** | +42 |

Values represent means ± SD of 6 mice per group.
*p < 0.05,
**p < 0.01 vs controls.

The invention claimed is:

1. Method of inhibiting the occurrence of hepatic steatosis and liver damage directly resulting therefrom in a healthy subject comprising providing said subject a diet with enhanced levels of a sphingolipid selected from the group consisting of:

(a) sphingolipids having the general formula (I)

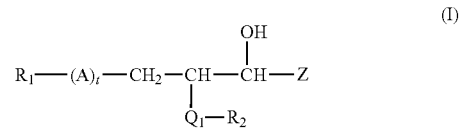

wherein

Z is $R_3$ or —CH(OH)—$R_3$;

A is sulphate, sulphonate, phosphate, phosphonate or —C(O)O—;

$R_1$ is H, hydroxyl, alditol, glycosyl, an alcohol, $C_1$-$C_6$ alkyl or amino acid;

$R_2$ is H or unsaturated or saturated ($C_1$-$C_{30}$) alkyl chain;

$R_3$ is unsaturated or saturated ($C_1$-$C_{30}$) alkyl chain;

$Q_1$ is a primary amine group (—$NH_2$), secondary amine group (—NH—) or an amide group (—NH—CO—); and t is 0 or 1;

(b) sphingolipids having the general formula (II)

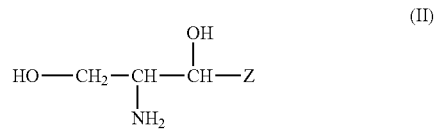

wherein

Z is $R_3$ or CH(OH)—$R_3$, and $R_3$ is an unsaturated or saturated ($C_1$-$C_{30}$) alkyl chain, or a precursor, a derivative or a pharmaceutically acceptable salt thereof; and (c) sphingolipids having the general formula (III)

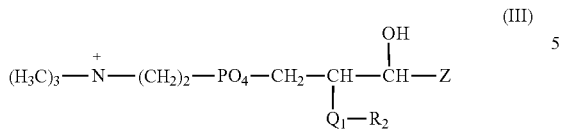

wherein
Z is $R_3$ or CH(OH)—$R_3$, preferably $R_3$;
$Q_1$ is a primary amine group (—$NH_2$), a secondary amine group (—NH—) or an amide group (—NH—CO—); preferably an amide group, and
$R_2$ is H or unsaturated or saturated ($C_1$-$C_{30}$) alkyl chain;
$R_3$ is an unsaturated or saturated ($C_1$-$C_{30}$) alkyl chain, preferably an unsaturated ($C_1$-$C_{30}$) alkyl chain;
or a pharmaceutically acceptable salt thereof.

2. Method of inhibiting the occurrence of hepatic steatosis and liver damage directly resulting therefrom in a healthy subject comprising administering to said subject a therapeutically effective amount of a pharmaceutical composition, said composition comprising a sphingolipid selected from the group consisting of:
(a) sphingolipids having the general formula (I)

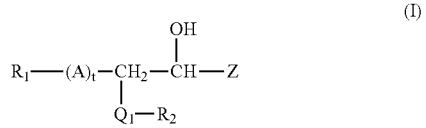

wherein
Z is $R_3$ or —CH(OH)—$R_3$;
A is sulphate, sulphonate, phosphate, phosphonate or —C(O)O—;
$R_1$ is H, hydroxyl, alditol, glycosyl, an alcohol, $C_1$-$C_6$ alkyl or amino acid;
$R_2$ is H or unsaturated or saturated ($C_1$-$C_{30}$) alkyl chain;
$R_3$ is unsaturated or saturated ($C_1$-$C_{30}$) alkyl chain;
$Q_1$ is a primary amine group (—$NH_2$), secondary amine group (—NH—) or an amide group (—NH—CO—); and
t is 0 or 1;

(b) sphingolipids having the general formula (II)

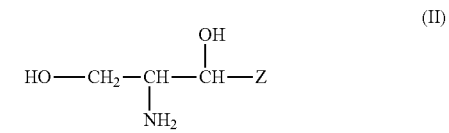

wherein
Z is $R_3$ or CH(OH)—$R_3$, and
$R_3$ is an unsaturated or saturated ($C_1$-$C_{30}$) alkyl chain, or a precursor, a derivative or a pharmaceutically acceptable salt thereof; and
(c) sphingolipids having the general formula (III)

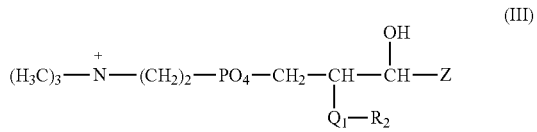

wherein
Z is $R_3$ or CH(OH)—$R_3$, preferably $R_3$;
$Q_1$ is a primary amine group (—$NH_2$), a secondary amine group (—NH—) or an amide group (—NH—CO—); preferably an amide group, and
$R_2$ is H or unsaturated or saturated ($C_1$-$C_{30}$) alkyl chain;
$R_3$ is an unsaturated or saturated ($C_1$-$C_{30}$) alkyl chain, preferably an unsaturated ($C_1$-$C_{30}$) alkyl chain;
or a pharmaceutically acceptable salt thereof and a pharmaceutically acceptable carrier, and optionally one or more excipients.

3. Method according to claim 1, wherein said sphingolipid is phytosphingosine, sphingosine, sphinganine, ceramide, glycosylceramide and/or sphingomyelin.

4. Method according to claim 3, wherein said sphingolipid is sphingosine.

5. Method according to claim 2, wherein said sphingolipid is phytosphingosine, sphingosine, sphinganine, ceramide, glycosylceramide and/or sphingomyelin.

6. Method according to claim 5, wherein said sphingolipid is sphingosine.

* * * * *

UNITED STATES PATENT AND TRADEMARK OFFICE
CERTIFICATE OF CORRECTION

PATENT NO. : 7,906,488 B2
APPLICATION NO. : 11/791876
DATED : March 15, 2011
INVENTOR(S) : Willem Ferdinand Nieuwenhuizen It is certified that error appears in the above-identified patent and that said Letters Patent is hereby corrected as shown below:

In the Specification

Column 21, line 54, "Perhexy-" should read -- Perhexi- --.

Signed and Sealed this
Fifth Day of August, 2014

Michelle K. Lee
*Deputy Director of the United States Patent and Trademark Office*